US012060411B2

(12) United States Patent
Nussenzweig et al.

(10) Patent No.: US 12,060,411 B2
(45) Date of Patent: Aug. 13, 2024

(54) NEUTRALIZING ANTI-SARS-CoV-2 ANTIBODIES

(71) Applicant: The Rockefeller University, New York, NY (US)

(72) Inventors: Michel Nussenzweig, New York, NY (US); Zijun Wang, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 17/575,246

(22) Filed: Jan. 13, 2022

(65) Prior Publication Data

US 2022/0227844 A1    Jul. 21, 2022

Related U.S. Application Data

(60) Provisional application No. 63/199,676, filed on Jan. 15, 2021.

(51) Int. Cl.

| C07K 16/10 | (2006.01) |
| A61K 39/42 | (2006.01) |
| A61K 45/06 | (2006.01) |
| G01N 33/569 | (2006.01) |

(52) U.S. Cl.
CPC .............. *C07K 16/10* (2013.01); *A61K 39/42* (2013.01); *A61K 45/06* (2013.01); *G01N 33/56983* (2013.01); *C07K 2317/31* (2013.01); *C07K 2317/35* (2013.01); *C07K 2317/76* (2013.01); *G01N 2333/165* (2013.01); *G01N 2800/26* (2013.01); *G01N 2800/52* (2013.01)

(58) Field of Classification Search
CPC .... C07K 16/10; C07K 2317/31; A61K 39/42; A61K 45/06
See application file for complete search history.

(56) References Cited

U.S. PATENT DOCUMENTS

| 11,053,304 | B1 * | 7/2021 | Glanville | ................. | A61P 31/14 |
| 11,634,477 | B2 * | 4/2023 | Nussenzweig | ......... | C07K 16/10 |
| | | | | | 424/133.1 |
| 2006/0121580 | A1 * | 6/2006 | Ter Meulen | ........... | C07K 16/10 |
| | | | | | 435/6.16 |
| 2021/0332110 | A1 | 10/2021 | Nussenzweig et al. | | |
| 2022/0195015 | A1 * | 6/2022 | Nussenzweig | ......... | A61K 39/42 |

OTHER PUBLICATIONS

Edwards et al. The Remarkable Flexibility of the Human Antibody Repertoire; Isolation of Over One Thousand Different Antibodies to a Single Protein, BLyS, J. Mol. Biol. 2003, 334:103-118. (Year: 2003).*
Lloyd et al. Modelling the human immune response: performance of a 1011 human antibody repertoire against a broad panel of therapeutically relevant antigens, Protein Engineering Design & Selection. 2009, 22;3: 159-168) (Year: 2009).*
Goel et al. Plasticity within the Antigen-Combining Site May Manifest as Molecular Mimicry in the Humoral Immune Response, The Journal of Immunology. 2004, 173:7358-7367 (Year: 2004).*
Kanyavuz et al. Breaking the law: unconventional strategies for antibody diversification, Nature Review Immunology. 2019, 19:355-368 (Year: 2019).*
Janeway et al., Immunology Third Edition, Garland Publishing Inc. 1997, Chapter 3, Structure of the Antibody Molecule and Immunoglobulin Genes, pp. 3:1-3:11, see entire selection (Year: 1997).*
Rudikoff et al., Single amino acid substitution altering antigen-binding specificity, PNAS, USA, 1982, 79: 1979-1983 (Year: 1982).*
Ter Meulen et al., Human Monoclonal Antibody Combination against SARS Coronavirus: Synergy and Coverage of Escape Mutants, PLoS Medicine, vol. 3, Issue 7, e237, Publication Date: Jul. 4, 2006 (Year: 2006).*
Tian et al., Potent binding of 2019 novel coronavirus spike protein by a SARS coronavirus-specific human monoclonal antibody, Emerging Microbes & Infections, 9:382-385, Published Date: Feb. 17, 2020 (Year: 2020).*
Koivunen et al., Principles of Immunochemical Techniques Used in Clinical Laboratories, Labmedicine, vol. 37, No. 8, pp. 490-497, Publication Date: Aug. 2006 (Year: 2006).*
Barnes Christopher O. et al: "SARS-CoV-2 neutralizing antibody structures inform therapeutic strategies", Nautre, vol. 588, No. 7839, Oct. 12, 2020 (Oct. 12, 2020), pp. 682-687.
Weisblum Yiska et al: "Escape from neutralizing antibodies by SARS-CoV-2 spike protein variants", ELIFE, vol. 9, Oct. 28, 2020 (Oct. 28, 2020), 31 pages.
Wang Bei et al: "Bivalent binding of a fully human IgG to the SARS-CoV-2 spike proteins reveals mechanisms of potent neutralization", bioRxiv, Jul. 15, 2020 (Jul. 15, 2020), 24 pages.
Robbiani Davide F et al: "Convergent antibody responses to SARS-CoV-2 in convalescent individuals", Nature, Nature Publishing Group UK, London, vol. 584, No. 7821, Jun. 18, 2020 (Jun. 18, 2020), pp. 437-442.
Wang Zijun et al: "mRNA vaccine-elicited antibodies to SARS-CoV-2 and circulating variants", Nature, Nature Publishing Group UK, London, vol. 592, No. 7855, Feb. 10, 2021 (Feb. 10, 2021), pp. 616-622.
Gaebler Christian et al: "Evolution of antibody immunity to SARS-CoV-2", Nature, vol. 591, No. 7851, Jan. 18, 2021 (Jan. 18, 2021), pp. 639-644.
Wang Zijun et al: "Naturally enhanced neutralizing breadth against SARS-CoV-2 one year after infection", Nature, Nature Publishing Group UK, London, vol. 595, No. 7867, Jun. 14, 2021 (Jun. 14, 2021), pp. 426-431.
Cho Alice et al: "Anti-SARS-CoV-2 receptor-binding domain antibody evolution after mRNA vaccination", Nature, Nature Publishing Group UK, London, vol. 600, No. 7889, Oct. 7, 2021 (Oct. 7, 2021), pp. 517-522.

(Continued)

*Primary Examiner* — Peter J Reddig
*Assistant Examiner* — Cheng Lu
(74) *Attorney, Agent, or Firm* — Fox Rothschild LLP

(57) ABSTRACT

This disclosure provides novel neutralizing anti-SARS-CoV-2 antibodies or antigen-binding fragments thereof. The disclosed anti-SARS-CoV-2 antibodies constitute a novel therapeutic strategy in protection from SARS-CoV-2 infections.

27 Claims, 13 Drawing Sheets

Specification includes a Sequence Listing.

(56) References Cited

OTHER PUBLICATIONS

Muecksch Frauke et al: "Affinity maturation of SARS-CoV-2 neutralizing antibodies confers potency, breadth, and resilience to viral escape mutations", Immunity, Cell Press, Amsterdam, NL, vol. 54, No. 8, Jul. 30, 2021 (Jul. 30, 2021), p. 1853.
De Gasparo Raoul et al: "Bispecific IgG neutralizes SARS-CoV-2 variants and prevents escape in mice", Nature, Nature Publishing Group UK, London, vol. 593, No. 7859, Mar. 25, 2021 (Mar. 25, 2021), pp. 424-428.
Invitation to Pay Additional Fees and, Where Applicable, Protest Fee (partial search report) mailed Apr. 19, 2022 in International Patent Application No. PCT/US2022/012299, 17 pages.

\* cited by examiner

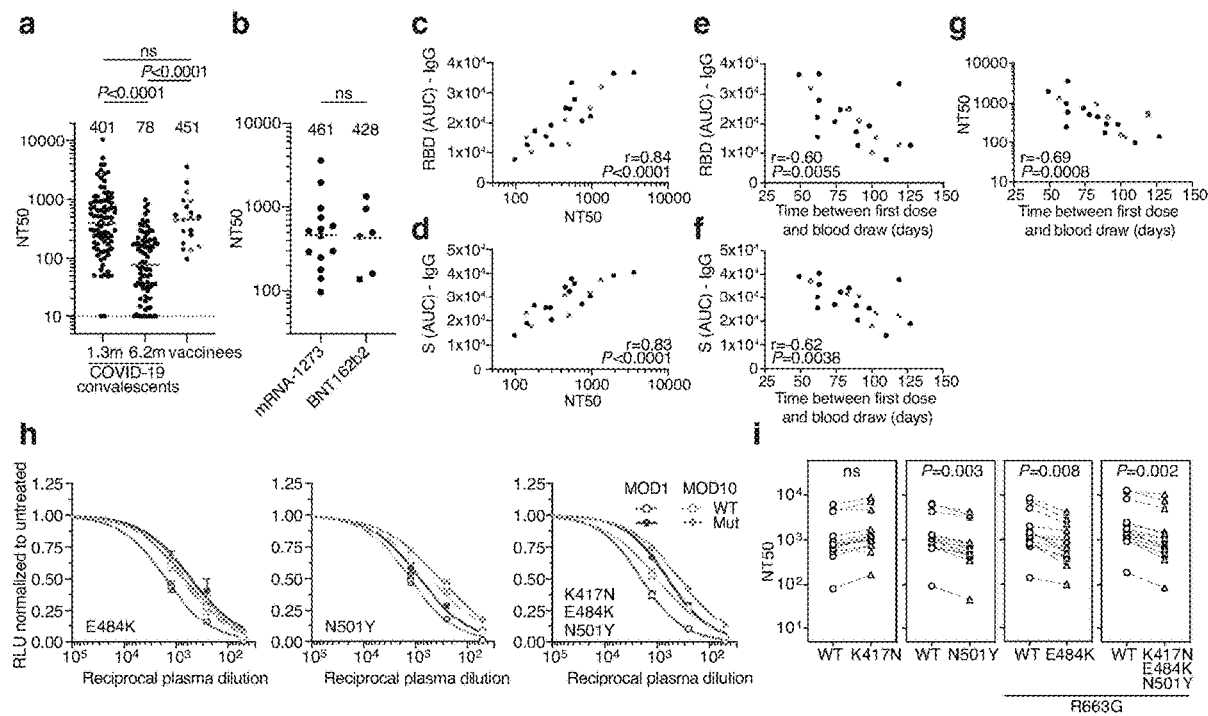
Figs. 1a, 1b, 1c, 1d, 1e, 1f, 1g, 1h, and 1i

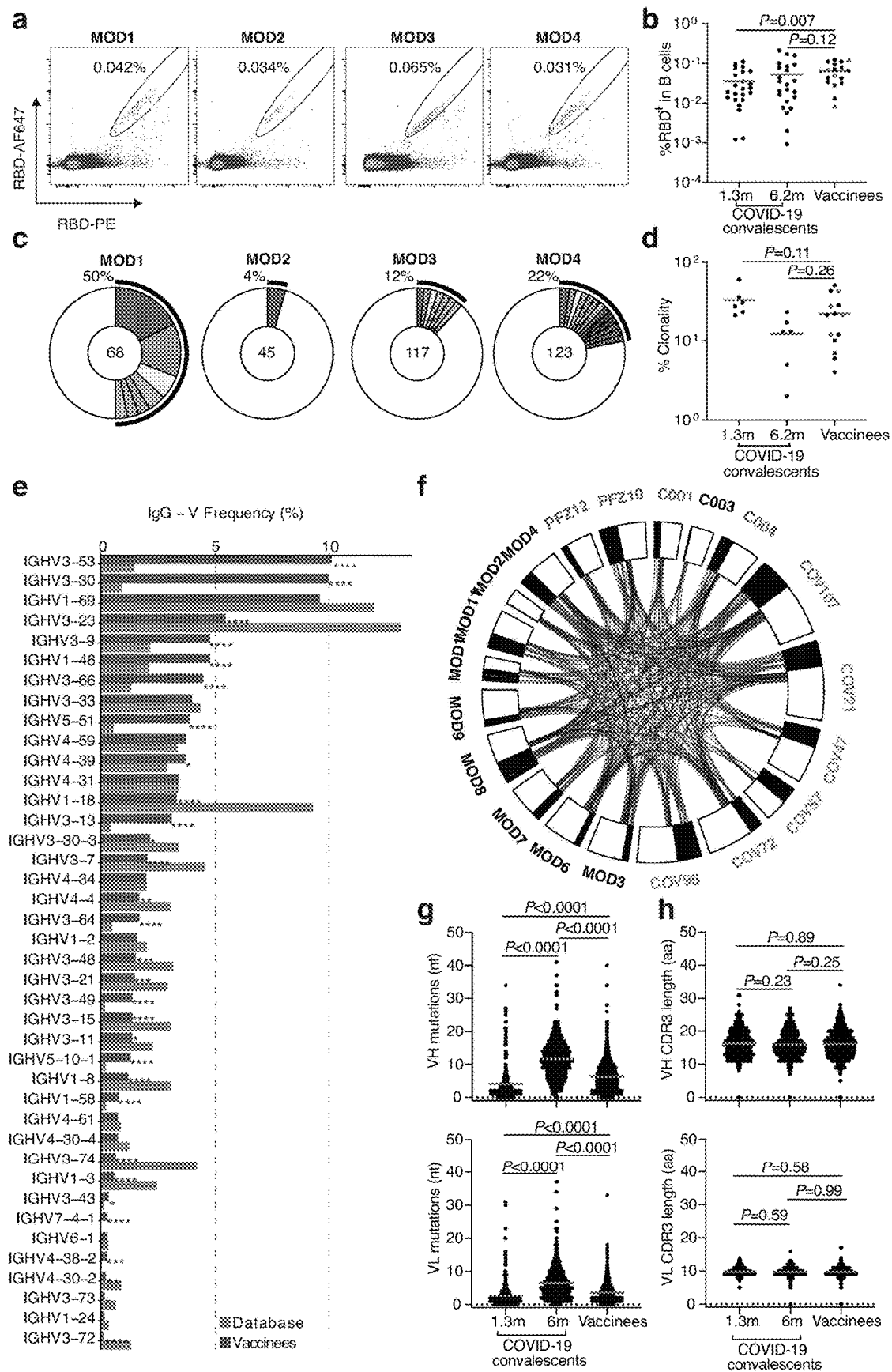
Figs. 2a, 2b, 2c, 2d, 2e, 2f, 2g, and 2h

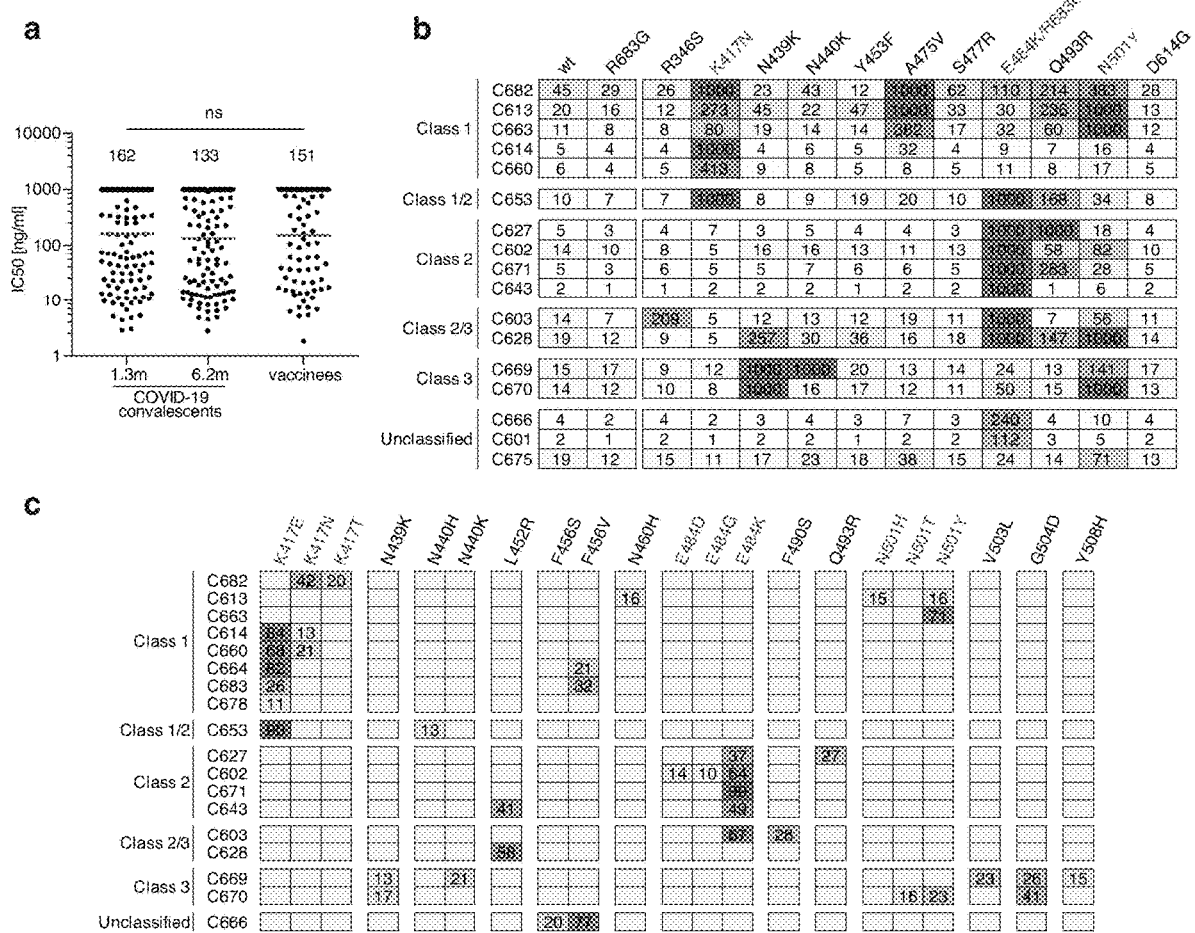
Figs. 3a, 3b, and 3c

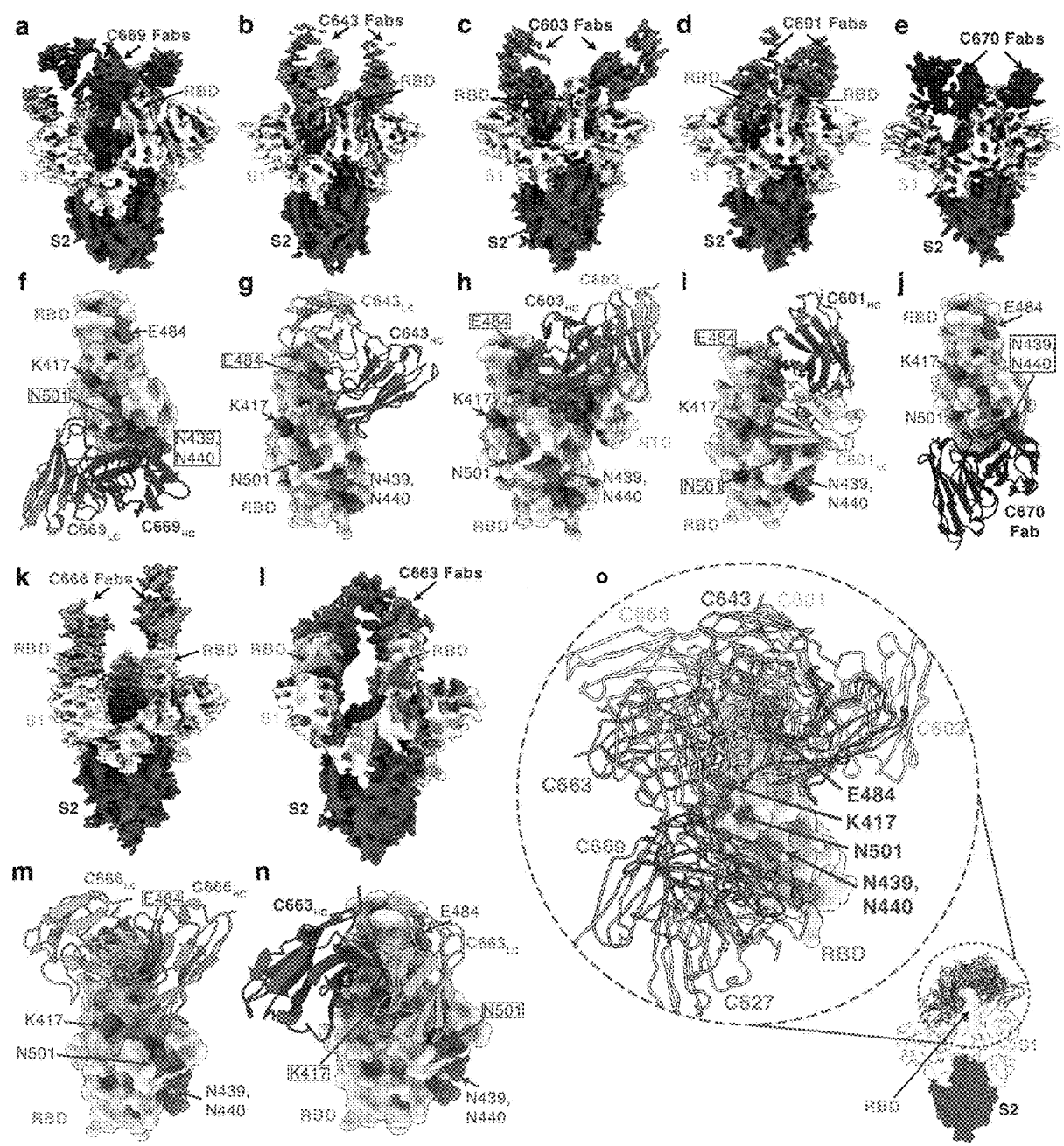
Figs. 4a, 4b, 4c, 4d, 4e, 4f, 4g, 4h, 4i, 4j, 4k, 4l, 4m, 4n, and 4o

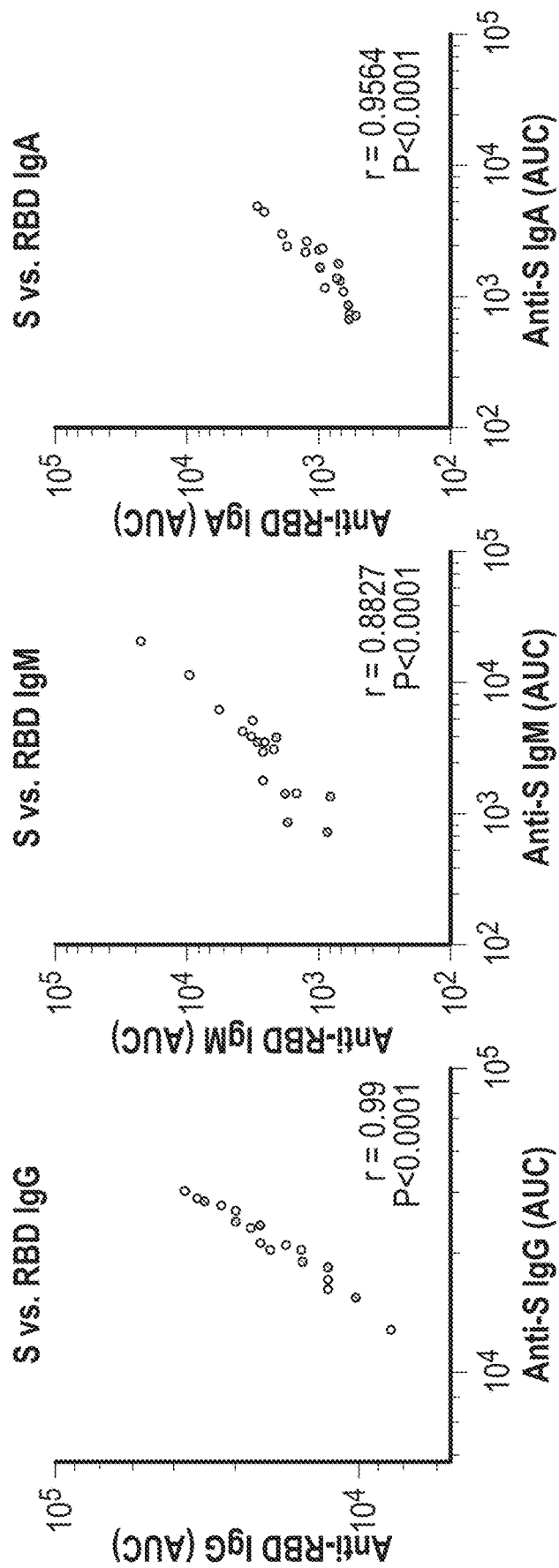

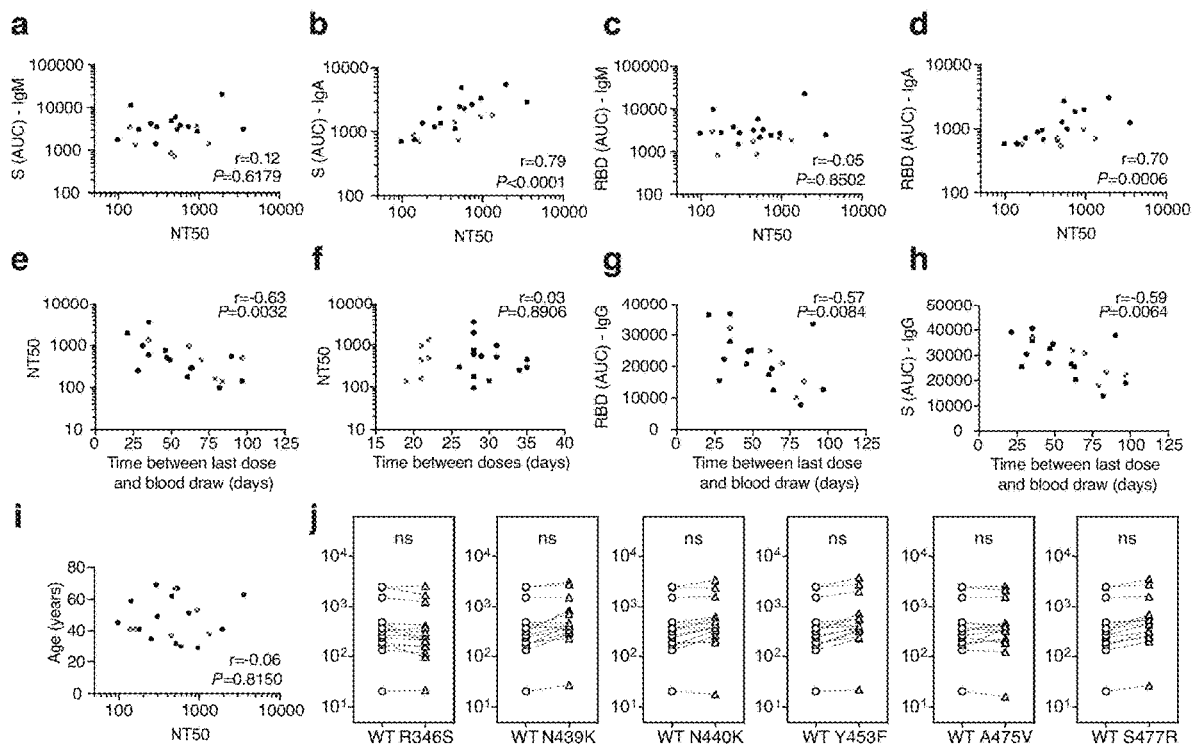
Figs. 6a, 6b, 6c, 6d, 6e, 6f, 6g, 6h, 6i, and 6j

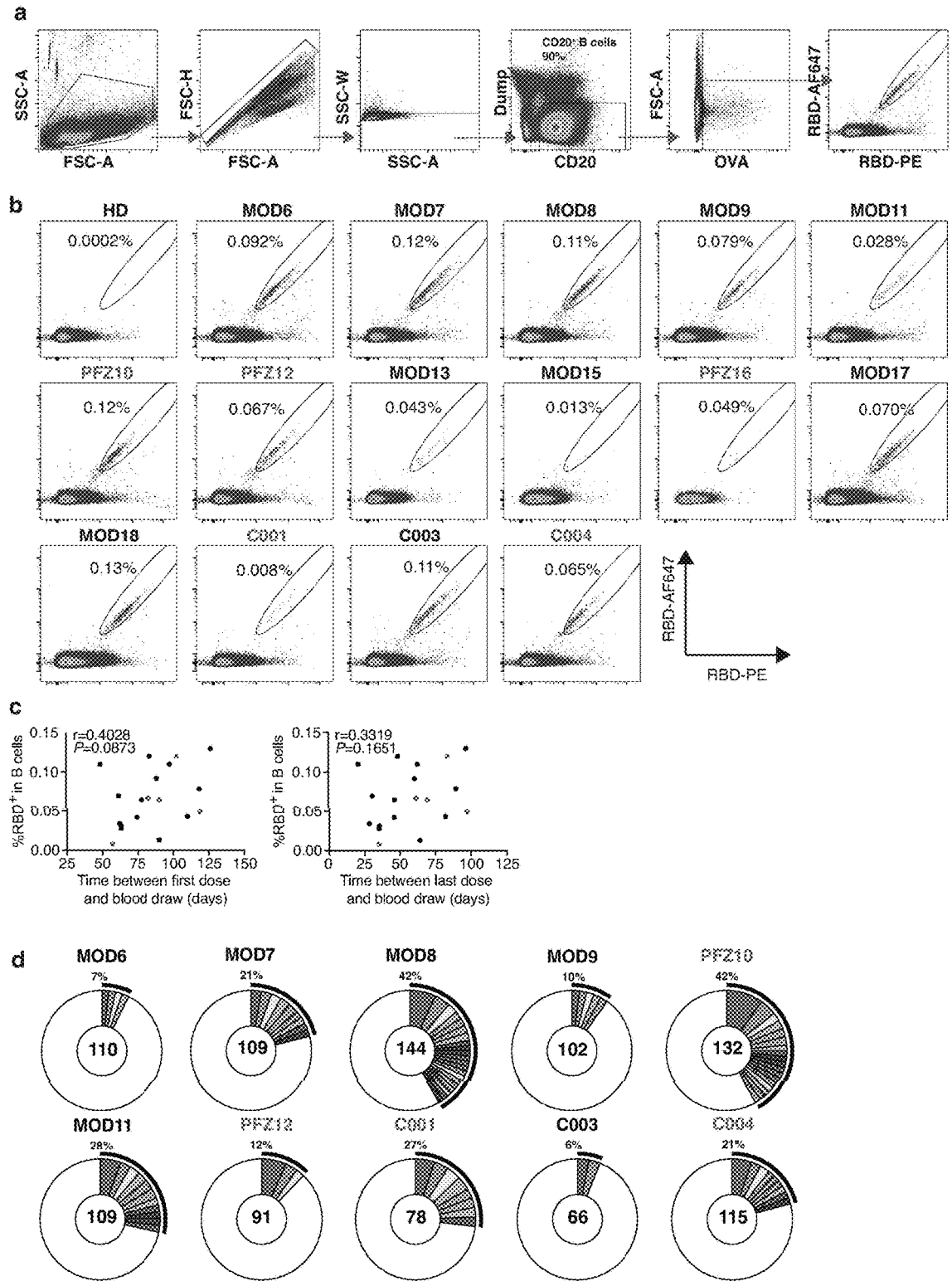
Figs. 7a, 7b, 7c, and 7d

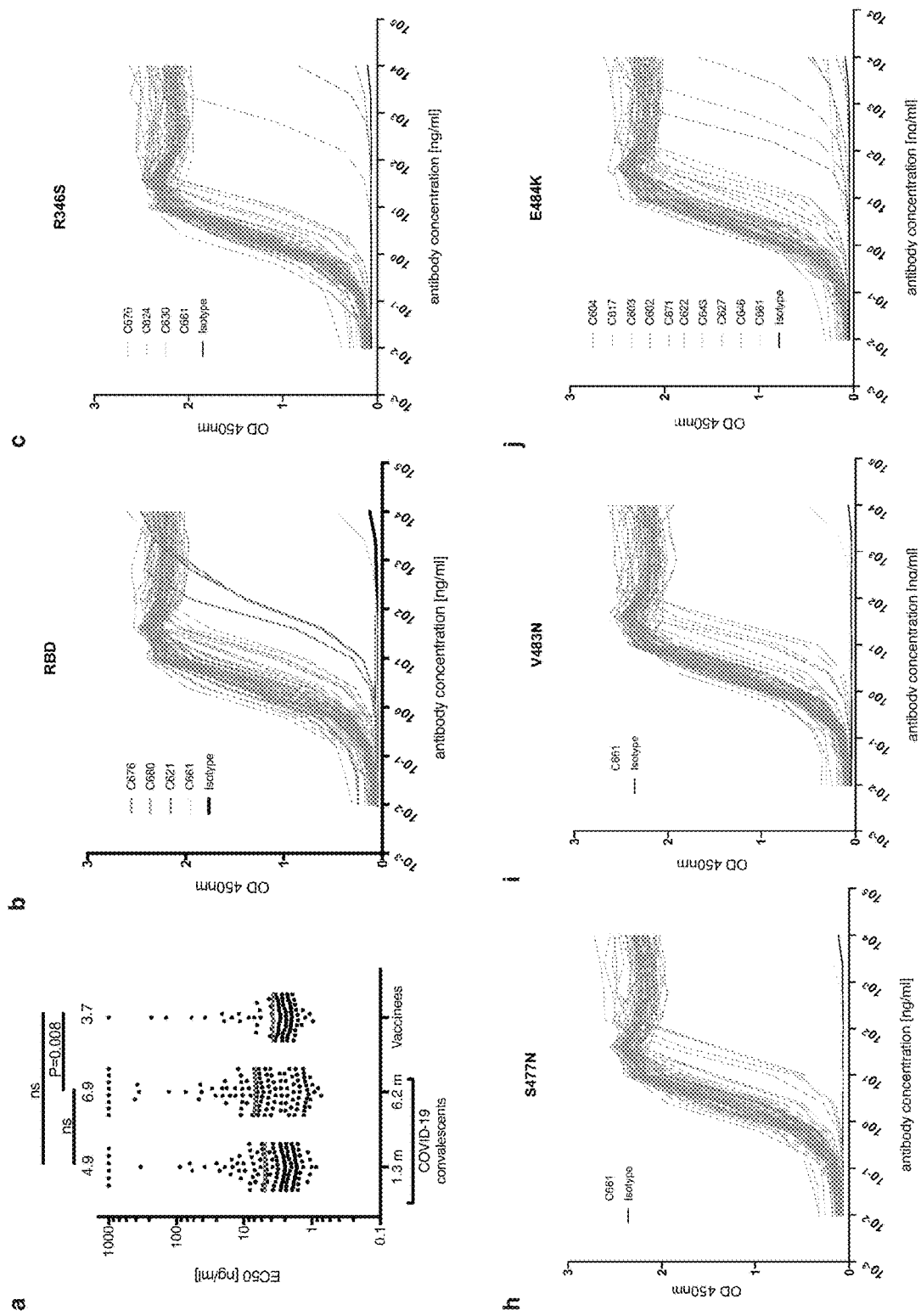
Figs. 10a, 10b, 10c, 10h, 10i, and 10j

NEUTRALIZING ANTI-SARS-CoV-2 ANTIBODIES

CROSS-REFERENCE TO RELATED APPLICATIONS

This application claims priority under 35 U.S.C. § 119(e) to U.S. Provisional Patent Application No. 63/199,676, filed Jan. 15, 2021. The foregoing application is incorporated by reference herein in its entirety.

STATEMENT REGARDING FEDERALLY FUNDED RESEARCH

This invention was made with government support under grant nos. P01-AI138398-S1 and 2U19AI111825 awarded by the National Institutes of Health. The government has certain rights in the invention.

REFERENCE TO SEQUENCE LISTING SUBMITTED ELECTRONICALLY

This application contains a sequence listing, which is submitted electronically via EFS-Web as an ASCII formatted sequence listing with a file name "Seq listing 070413.20672_ST25" and a creation date of Jan. 12, 2022, and having a size of 3,820 kb. The sequence listing submitted via EFS-Web is part of the specification and is herein incorporated by reference in its entirety.

FIELD OF THE INVENTION

The present invention relates to antibodies directed to epitopes of SARS-CoV-2 Coronavirus 2 ("SARS-CoV-2"). The present invention further relates to the preparation and use of neutralizing antibodies directed to the SARS-CoV-2 spike (S) glycoproteins for the prevention and treatment of SARS-CoV-2 infection.

BACKGROUND

SARS-CoV-2 is the virus that causes coronavirus disease 2019 (COVID-19). It contains four structural proteins, including spike (S), envelope (E), membrane (M), and nucleocapsid (N) proteins. Among them, S protein plays the most important role in viral attachment, fusion, and entry, and it serves as a target for development of antibodies, entry inhibitors, and vaccines. The S protein mediates viral entry into host cells by first binding to a host receptor through the receptor-binding domain (RBD) in the S1 subunit and then fusing the viral and host membranes through the S2 subunit. SARS-CoV and MERS-COV RBDs recognize different receptors. SARS-CoV recognizes angiotensin-converting enzyme 2 (ACE2) as its receptor, whereas MERS-COV recognizes dipeptidyl peptidase 4 (DPP4) as its receptor. Similar to SARS-CoV, SARS-CoV-2 also recognizes ACE2 as its host receptor binding to viral S protein. SARS-CoV-2 has infected 45 million individuals and is responsible for over 1 million deaths to date. There is a pressing need for agents for treating or preventing SARS-CoV-2 infection.

SUMMARY

This disclosure addresses the need mentioned above in a number of aspects by providing neutralizing anti-SARS-CoV-2 antibodies or antigen-binding fragments thereof.

In one aspect, this disclosure provides an isolated anti-SARS-CoV-2 antibody or antigen-binding fragment thereof that binds specifically to a SARS-CoV-2 antigen. In some embodiments, the SARS-CoV-2 antigen comprises a Spike (S) polypeptide, such as a S polypeptide of a human or an animal SARS-CoV-2. In some embodiments, the SARS-CoV-2 antigen comprises the receptor-binding domain (RBD) of the S polypeptide. In some embodiments, the RBD comprises amino acids 319-541 of the S polypeptide.

In some embodiments, the antibody or antigen-binding fragment thereof is capable of neutralizing a plurality of SARS-CoV-2 strains.

In some embodiments, the antibody or antigen-binding fragment thereof comprises: three heavy chain complementarity determining regions (HCDRs) (HCDR1, HCDR2, and HCDR3) of a heavy chain variable region having the amino acid sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, or 167; and three light chain CDRs (LCDR1, LCDR2, and LCDR3) of a light chain variable region having the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168.

In some embodiments, the antibody or antigen-binding fragment thereof comprises: (i) a heavy chain variable region having an amino acid sequence with at least 75% identity to one selected from those in Table 2 or 4; and/or (ii) a light chain variable region having an amino acid sequence with at least 75% identity to one selected from those in Table 2 or 4.

In some embodiments, the antibody or antigen-binding fragment thereof comprises: (i) a heavy chain variable region having the amino acid sequence of one selected from those in Table 2 or 4; and/or (ii) a light chain variable region having the amino acid sequence of one selected from those in Table 2 or 4.

In some embodiments, the antibody or antigen-binding fragment thereof comprises a heavy chain variable region and a light chain variable region that comprise the amino acid sequence pair selected from those in Table 2 or 4.

In some embodiments, the antibody or antigen-binding fragment thereof comprises: a heavy chain variable region having an amino acid sequence with at least 75% identity to the amino acid sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, or 167; or having the amino acid sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, or 167; and a light chain variable region having an amino acid sequence with at least 75% identity to the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168; or having the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168.

In some embodiments, the antibody or antigen-binding fragment thereof comprises a heavy chain variable region and a light chain variable region comprise the respective amino acid sequences of SEQ ID NOs: 1-2, 3-4, 5-6, 7-8, 9-10, 11-12, 13-14, 15-16, 17-18, 19-20, 21-22, 23-24, 25-26, 27-28, 29-30, 31-32, 33-34, 35-36, 37-38, 39-40, 41-42, 43-44, 45-46, 47-48, 49-50, 51-52, 53-54, 55-56, 57-58, 59-60, 61-62, 63-64, 65-66, 67-68, 69-70, 71-72, 73-74, 75-76, 77-78, 79-80, 81-82, 83-84, 85-86, 87-88, 89-90, 91-92, 93-94, 95-96, 97-98, 99-100, 101-102, 103-104, 105-106, 107-108, 109-110, 111-112, 113-114, 115-116, 117-118, 119-120, 121-122, 123-124, 125-126, 127-128, 129-130, 131-132, 133-134, 135-136, 137-138, 139-140, 141-142, 143-144, 145-146, 147-148, 149-150, 151-152, 153-154, 155-156, 157-158, 159-160, 161-162, 163-164, 165-166, or 167-168.

In some embodiments, the antibody or antigen-binding fragment thereof is a multivalent antibody that comprises (a) a first target binding site that specifically binds to an epitope within the S polypeptide, and (b) a second target binding site that binds to a different epitope on the S polypeptide or a different molecule. In some embodiments, the multivalent antibody is a bivalent or bispecific antibody.

In some embodiments, the antibody or the antigen-binding fragment thereof further comprises a variant Fc constant region. In some embodiments, the antibody is a monoclonal antibody. In some embodiments, the antibody is a chimeric antibody, a humanized antibody, or a humanized monoclonal antibody. In some embodiments, the antibody is a single-chain antibody, Fab or Fab2 fragment.

In some embodiments, the antibody or antigen-binding fragment thereof is detectably labeled or conjugated to a toxin, a therapeutic agent, a polymer, a receptor, an enzyme, or a receptor ligand. In some embodiments, the polymer is polyethylene glycol (PEG).

For example, an antibody of the invention may be coupled to a toxin. Such antibodies may be used to treat animals, including humans, that are infected with the virus that is etiologically linked to SARS-CoV-2. For example, an antibody that binds to the spike protein of the coronavirus that is etiologically linked to SARS-CoV-2 may be coupled to a tetanus toxin and administered to an animal suffering from infection by the aforementioned virus. The toxin-coupled antibody is thought to bind to a portion of a spike protein presented on an infected cell, and then kill the infected cell.

An antibody of the invention may be coupled to a detectable tag. Such antibodies may be used within diagnostic assays to determine if an animal, such as a human, is infected with SARS-CoV-2. Examples of detectable tags include fluorescent proteins (i.e., green fluorescent protein, red fluorescent protein, yellow fluorescent protein), fluorescent markers (i.e., fluorescein isothiocyanate, rhodamine, texas red), radiolabels (i.e., 3H, 32P, 125I), enzymes (i.e., β-galactosidase, horseradish peroxidase, β-glucuronidase, alkaline phosphatase), or an affinity tag (i.e., avidin, biotin, streptavidin).

In another aspect, this disclosure provides a pharmaceutical composition comprising: the antibody or antigen-binding fragment thereof of any one of the preceding claims and optionally a pharmaceutically acceptable carrier or excipient.

In some embodiments, the pharmaceutical comprises two or more of the antibody or antigen-binding fragment thereof described above, such as any combinations of the antibody or antigen-binding fragment thereof comprising a heavy chain and a light chain that comprise the respective amino acid sequences of one selected from those in Table 2 or 4.

In some embodiments, the two or more of the antibody or antigen-binding fragment thereof comprise: (1) a first antibody set comprising: (i) a first antibody or antigen-binding fragment thereof comprising a heavy chain variable region and a light chain variable region comprising the respective amino acid sequences of a first antibody selected from those in Table 2 or 4; and (ii) a second antibody or antigen-binding fragment thereof comprising a heavy chain variable region and a light chain variable region comprising the respective amino acid sequences of a second antibody selected from those in Table 2 or 4; or (2) a second antibody set comprising: (a) a third antibody or antigen-binding fragment thereof comprising a heavy chain variable region and a light chain variable region comprising the respective amino acid sequences of antibody selected from those in Table 2 or 4; and (b) a fourth antibody or antigen-binding fragment thereof comprising a heavy chain variable region and a light chain variable region comprising the respective amino acid sequences of an antibody selected from those in Table 2 or 4, wherein the third antibody is different from the fourth antibody.

In some embodiments, the pharmaceutical composition further comprises a second therapeutic agent. In some embodiments, the second therapeutic agent comprises an anti-inflammatory drug or an antiviral compound. In some embodiments, the antiviral compound comprises: a nucleoside analog, a peptoid, an oligopeptide, a polypeptide, a protease inhibitor, a 3C-like protease inhibitor, a papain-like protease inhibitor, or an inhibitor of an RNA dependent RNA polymerase. In some embodiments, the antiviral compound may include: acyclovir, gancyclovir, vidarabine, foscarnet, cidofovir, amantadine, ribavirin, trifluorothymidine, zidovudine, didanosine, zalcitabine, or an interferon. In some embodiments, the interferon is an interferon-α or an interferon-β.

Also within the scope of this disclosure is use of the pharmaceutical composition, as described above, in the preparation of a medicament for the diagnosis, prophylaxis, treatment, or combination thereof of a condition resulting from a SARS-CoV-2.

In another aspect, this disclosure also provides (i) a nucleic acid molecule encoding a polypeptide chain of the antibody or antigen-binding fragment thereof described above; (ii) a vector comprising the nucleic acid molecule as described; and (iii) a cultured host cell comprising the vector as described.

Also provided is a method for producing a polypeptide, comprising: (a) obtaining the cultured host cell as described; (b) culturing the cultured host cell in a medium under conditions permitting expression of a polypeptide encoded by the vector and assembling of an antibody or fragment thereof; and (c) purifying the antibody or fragment from the cultured cell or the medium of the cell.

In another aspect, this disclosure provides a kit comprising a pharmaceutically acceptable dose unit of the antibody or antigen-binding fragment thereof or the pharmaceutical composition as described above. Also within the scope of this disclosure is a kit for the diagnosis, prognosis, or monitoring of the treatment of SARS-CoV-2 in a subject, comprising: the antibody or antigen-binding fragment thereof as described; and a least one detection reagent that binds specifically to the antibody or antigen-binding fragment thereof.

In yet another aspect, this disclosure further provides a method of neutralizing SARS-CoV-2 in a subject. The method comprises administering to a subject in need thereof a therapeutically effective amount of the antibody or antigen-binding fragment thereof or a therapeutically effective amount of the pharmaceutical composition, as described herein.

In yet another aspect, this disclosure additionally provides a method of preventing or treating a SARS-CoV-2 infection. The method comprises administering to a subject in need thereof a therapeutically effective amount of the antibody or antigen-binding fragment thereof or a therapeutically effective amount of the pharmaceutical composition, as described herein.

In some embodiments, the method of neutralizing SARS-CoV-2 in a subject comprises administering to a subject in need thereof a therapeutically effective amount of a first antibody or antigen-binding fragment thereof and a second antibody or antigen-binding fragment thereof of the antibody or antigen-binding fragment, as described above, wherein the first antibody or antigen-binding fragment thereof and the second antibody or antigen binding fragment thereof exhibit synergistic activity or a therapeutically effective amount of the pharmaceutical composition described above.

In some embodiments, the method of preventing or treating a SARS-CoV-2 infection, comprising administering to a subject in need thereof a therapeutically effective amount of a first antibody or antigen-binding fragment thereof and a second antibody or antigen-binding fragment thereof of the antibody or antigen-binding fragment, as described above, wherein the first antibody or antigen-binding fragment thereof and the second antibody or antigen binding fragment thereof exhibit synergistic activity or a therapeutically effective amount of the pharmaceutical composition described above. In some embodiments, the first antibody or antigen-binding fragment thereof is administered before, after, or concurrently with the second antibody or antigen-binding fragment thereof.

In some embodiments, the first antibody or antigen-binding fragment thereof and the second antibody or antigen-binding fragment thereof can be any combinations of the antibody or antigen-binding fragment thereof comprising a heavy chain and a light chain that comprise the respective amino acid sequences of an antibody selected from those in Table 2 or 4.

In some embodiments, the second therapeutic agent comprises an anti-inflammatory drug or an antiviral compound. In some embodiments, the antiviral compound comprises a nucleoside analog, a peptoid, an oligopeptide, a polypeptide, a protease inhibitor, a 3C-like protease inhibitor, a papain-like protease inhibitor, or an inhibitor of an RNA dependent RNA polymerase. In some embodiments, the antiviral compound may include: acyclovir, gancyclovir, vidarabine, foscarnet, cidofovir, amantadine, ribavirin, trifluorothymidine, zidovudine, didanosine, zalcitabine, or an interferon. In some embodiments, the interferon is an interferon-$\alpha$ or an interferon-$\beta$.

In some embodiments, the antibody or antigen-binding fragment thereof is administered before, after, or concurrently with the second therapeutic agent or therapy. In some embodiments, the antibody or antigen-binding fragment thereof is administered to the subject intravenously, subcutaneously, or intraperitoneally. In some embodiments, the antibody or antigen-binding fragment thereof is administered prophylactically or therapeutically.

In another aspect, this disclosure further provides a method for detecting the presence of SARS COV-2 in a sample comprising the steps of: (i) contacting a sample with the antibody or antigen-binding fragment thereof described above; and (ii) determining binding of the antibody or antigen-binding fragment to one or more SARS COV-2 antigens, wherein binding of the antibody to the one or more SARS COV-2 antigens is indicative of the presence of SARS COV-2 in the sample. In some embodiments, the sample is a blood sample.

In some embodiments, the SARS-CoV-2 antigen comprises a S polypeptide, such as a S polypeptide of a human or an animal SARS-CoV-2. In some embodiments, the SARS-CoV-2 antigen comprises the receptor-binding domain (RBD) of the S polypeptide. In some embodiments, the RBD comprises amino acids 319-541 of the S polypeptide.

In some embodiments, the antibody or antigen-binding fragment thereof is conjugated to a label. In some embodiments, the step of detecting comprises contacting a secondary antibody with the antibody or antigen-binding fragment thereof and wherein the secondary antibody comprises a label. In some embodiments, the label includes a fluorescent label, a chemiluminescent label, a radiolabel, and an enzyme.

In some embodiments, the step of detecting comprises detecting fluorescence or chemiluminescence. In some embodiments, the step of detecting comprises a competitive binding assay or ELISA.

In some embodiments, the method further comprises binding the sample to a solid support. In some embodiments, the solid support includes microparticles, microbeads, magnetic beads, and an affinity purification column.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

BRIEF DESCRIPTION OF THE DRAWINGS

FIGS. 1a, 1b, 1c, 1d, 1e, 1f, 1g, 1h, and 1i are a set of diagrams showing plasma neutralizing activity of the neutralizing antibodies. FIG. 1a shows SARS-CoV-2 pseudovirus neutralization assay. $NT_{50}$ values for COVID-19 convalescent plasma were measured at 1.3 months and 6.2 months as well as plasma from mRNA-vaccinees. $NT_{50}$ values lower than 10 were plotted at 10. Mean of 2 independent experiments. Indicated values represent geometric mean $NT_{50}$ values. Statistical significance was determined using a two-tailed Mann-Whitney U-test. FIG. 1b shows $NT_{50}$ values for Moderna and Pfizer/BioNTech vaccine recipients. Bars and indicated values represent geometric mean $NT_{50}$ values. Statistical significance was determined using a two-tailed Mann-Whitney U-test. FIG. 1c shows anti-RBD IgG AUC (Y axis) plotted against $NT_{50}$ (X axis) r=0.84, p<0.0001. FIG. 1d shows anti-S IgG AUC (Y axis) plotted against $NT_{50}$ (X axis) r=0.83, p<0.0001. FIG. 1e shows anti-RBD IgG AUC (Y axis) plotted against time between the first dose and blood draw (X axis) r=−0.60 p=0.0055. FIG. 1f shows anti-S IgG AUC (Y axis) plotted against time between the first dose and blood draw (X axis) r=−0.62 p=0.0038. FIG. 1g shows $NT_{50}$ (Y axis) plotted against time between the first dose and blood draw (X axis) r=−0.69 p=0.0008. The r and p values for correlations in FIGS. 1c-g were determined by two-tailed Spearman's. FIG. 1h shows examples of neutralization assays, comparing the sensitivity of pseudotyped viruses with WT and RBD mutant SARS-CoV-2 S proteins to vaccinee plasma. FIG. 1i shows $NT_{50}$ values for vaccinee plasma (n=15) neutralization of pseudotyped viruses with WT and the indicated RBD-mutant SARS-CoV-2 S proteins. Statistical significance was determined. All experiments were performed a minimum of 2 times.

FIGS. 2a, 2b, 2c, 2d, 2e, 2f, 2g, and 2h are a set of diagrams showing characterization of memory B cell antibodies. FIG. 2a shows representative flow cytometry plots showing dual AlexaFluor-647-RBD and PE-RBD binding B cells for 4 vaccinees. FIG. 2b, as in FIG. 2a, shows a dot plot summarizing the percentage of RBD binding B cells in 19 vaccinees, in comparison to a cohort of infected individuals assays 1.3 and 6.2 months after infection. The horizontal bars indicate mean values. Statistical significance was determined using a two-tailed Mann-Whitney U-tests. FIG. 2c shows pie charts depicting the distribution of antibody sequences from the 4 individuals in FIG. 2a. The number in the inner circle indicates the number of sequences analyzed. Pie slice size is proportional to the number of clonally related sequences. The black outline indicates the frequency of clonally expanded sequences. FIG. 2d, as in FIG. 2c, is a graph showing relative clonality among 14 vaccinees assayed. Statistical significance was determined using a two-tailed Mann-Whitney U-tests. FIG. 2e is a graph showing relative abundance of human IGVH genes Sequence Read Archive accession SRP010970 and vaccinees. A two-sided binomial test was used to compare the frequency distributions; significant differences are denoted with stars. FIG. 2f shows clonal relationships between sequences from 14 vaccinated individuals (Moderna and Pfizer in Table 2) and naturally infected individuals. Interconnecting lines indicate the relationship between antibodies that share V and J gene segment sequences at both IGH and IGL. FIG. 2g shows number of somatic nucleotide mutations in the IGVH (top) and IGVL (bottom) in vaccinee antibodies (Table 2) compared to natural infection obtained 1.3 or 6.2 months after infection. Statistical significance was determined using the two-tailed Mann-Whitney U-tests, and the horizontal bars indicate mean values. FIG. 2h, as in FIG. 2g, but for CDR3 length.

FIGS. 3a, 3b, and 3c are a set of diagrams showing anti-SARS-CoV-2 RBD monoclonal antibody neutralizing activity. FIG. 3a shows the results of a SARS-CoV-2 pseudovirus neutralization assay. $IC_{50}$ values for antibodies cloned from COVID-19 convalescent patients were measured at 1.3 and 6.2 months as well as antibodies cloned from mRNA-vaccinees. Antibodies with $IC_{50}$ values above 1000 ng/ml were plotted at 1000 ng/ml. Mean of 2 independent experiments. Indicated values represent geometric mean $IC_{50}$ values in ng/ml. Statistical significance was determined using a two-tailed Mann-Whitney U-test. FIG. 3b shows $IC_{50}$ values for 17 selected mAbs for neutralization of wild type and the indicated mutant SARS-CoV-2 pseudoviruses. FIG. 3c shows that antibody selection pressure can drive emergence of S variants in cell culture; the percentage of sequence reads bearing the indicated RBD mutations after a single passage of rVSV/SARS-CoV-2 in the presence of the indicated antibodies is tabulated. Values represent the decimal frequency with which each mutation occurs as assessed by sequencing.

FIGS. 4a, 4b, 4c, 4d, 4e, 4f, 4g, 4h, 4i, 4j, 4k, 4l, 4m, and 4n are a set of diagrams showing cryo-EM reconstructions of Fab-S complexes. Cryo-EM densities for Fab-S complexes (FIGS. 4a-e; FIGS. 4k-l) and close-up views of antibody footprints on RBDs (FIGS. 4f-j; FIGS. 4m-n) are shown for neutralizing mAbs. As expected, due to Fab inter-domain flexibility, cryo-EM densities (FIGS. 4a-e; FIGS. 4k-l) were weak for the Fab $C_H$-$C_L$ domains. Antibody footprints on RBDs (FIGS. 4f-j; FIGS. 4m-n) are presented as Fab $V_H$-$V_L$ domains (cartoon) complexed with the RBD (surface). FIGS. 4a and 4f, C669; FIGS. 4b and 4g, C643; FIGS. 4c and 4h, C603; FIGS. 4d and 4i, C601; FIGS. 4e and 4j, C670; FIGS. 4k and 4m, C666; and FIGS. 4l and 4n, C669. RBD residues K417, N439, N440, E484, and N501 are highlighted. The N343 glycan is shown as a teal sphere. FIG. 4o shows a composite model illustrating targeted epitopes of RBD-specific neutralizing mAbs (shown as $V_H$-$V_L$ domains from panels FIGS. 4a-1) elicited from mRNA vaccines.

FIGS. 5a, 5b, 5c, 5d, 5e, 5f, 5g, 5h, and 5i are a set of diagrams showing characterization of plasma antibodies against SARS-CoV-2. FIGS. 5a, 5b, 5c, 5d, 5e, and 5f show the results of ELISAs measuring plasma reactivity to S (FIGS. 5a, 5c, and 5e) and RBD protein (FIGS. 5b, 5d, and 5f) of 20 vaccinees (grey curves) and 8 controls (black curves). FIG. 5a, Anti-S IgG. FIG. 5b, Anti-RBD IgG. FIG. 5c, Anti-S IgM. FIG. 5d, Anti-RBD IgM. FIG. 5e, Anti-S IgA. FIG. 5f, Anti-RBD IgA. Left, optical density at 450 nm (OD 450 nm) for the indicated reciprocal plasma dilutions. Right, normalized area under the curve (AUC) values for the 8 controls and 20 vaccinees. Horizontal bars indicate geometric mean. Statistical significance was determined using the two-tailed Mann-Whitney U-test. Average of two or more experiments. FIGS. 5g, 5h, and 5i show correlations of plasma antibodies measurements. FIG. 5g shows normalized AUC for IgG anti-S plotted against normalized AUC for IgG anti-RBD. FIG. 5h shows normalized AUC for IgM anti-S plotted against normalized AUC for IgM anti-RBD. FIG. 5i shows normalized AUC for IgA anti-S plotted against normalized AUC for IgA anti-RBD. The r and p values in FIGS. 5g-i were determined with the two-tailed Spearman's correlation test.

FIGS. 6a, 6b, 6c, 6d, 6e, 6f, 6g, 6h, 6i, and 6j are a set of diagrams showing plasma neutralizing activity and binding correlations. FIG. 6a shows anti-S IgM AUC (Y axis) plotted against $NT_{50}$ (X axis) r=0.12, p<0.6179. FIG. 6b shows anti-S IgA AUC (Y axis) plotted against $NT_{50}$ (X axis) r=0.79, p<0.0001. FIG. 6c shows anti-RBD IgM AUC (Y axis) plotted against $NT_{50}$ (X axis) r=−0.05 p=0.8502. FIG. 6d shows anti-RBD IgA AUC (Y axis) plotted against $NT_{50}$ (X axis) r=0.70 p=0.0006. FIG. 6e shows $NT_{50}$ (Y axis) plotted against time between last dose and blood draw (X axis) r=−0.63 p=0.0032. FIG. 6f shows $NT_{50}$ (Y axis) plotted against time between doses (X axis) r=0.03 p=0.8906. FIG. 6g shows anti-RBD IgG AUC (Y axis) plotted against time between last dose and blood draw (X axis) r=−0.57 p=0.0084. FIG. 6h shows anti-S IgG AUC (Y axis) plotted against time between last dose and blood draw (X axis) r=−0.59 p=0.0064. FIG. 6i shows Age (Y axis) plotted against $NT_{50}$ (X axis) r=−0.06 p=0.8150. The r and p values were determined by two-tailed Spearman's. FIG. 6j shows $NT_{50}$ values for vaccinee plasma neutralization of pseudotyped viruses with WT and the indicated RBD-mutant SARS-CoV-2 S proteins.

FIGS. 7a, 7b, 7c, and 7d are a set of diagrams showing the results of flow cytometry. FIG. 7a shows gating strategy used for cell sorting. Gating was on singlets that were CD20+ and CD3−CD8−CD16−OVA−. Sorted cells were RBD-PE+ and RBD-AF647+. FIG. 7b shows the results of flow cytometry depicting the percentage of RBD-double positive memory B cells from a pre-COVID-19 control (HD) and 15 vaccinees. FIG. 7c shows the percentage of RBD-binding memory B cells in vaccinees (Y axis) plotted against time between the first dose and blood draw (X axis) r=0.4028 p=0.0873 (left panel), and between last dose and blood draw (X axis) r=0.3319 p=0.1651 (right panel). FIG. 7d shows pie charts depicting the distribution of antibody sequences from 10 individuals in FIG. 7b. The number in the inner circle indicates the number of sequences analyzed. Pie slice size is proportional to the number of clonally related sequences. The black outline indicates the frequency of clonally expanded sequences. The r and p values for correlations in FIG. 7c was determined by two-tailed Spearman's.

FIG. 8a is a graph showing relative abundance of human IGVK (left) and IgVL (right) genes of Sequence Read Archive accession SRP010970 and vaccinees. Two-sided binomial tests with unequal variance were used to compare the frequency distributions, significant differences are denoted with stars. (*p<0.05, p<0.01, *p<0.001, ****=p<0.0001). FIG. 8b shows sequences from 14 individuals (Table 2) with clonal relationships depicted as in FIG. 8a. Interconnecting lines indicate the relationship between antibodies that share V and J gene segment sequences at both IGH and IGL.

FIG. 9a shows number of somatic nucleotide mutations in both the IGVH and IGVL in 14 participants (left). For each individual, the number of the amino acid length of the CDR3s at the IGVH and IGVL is shown (right). The horizontal bars indicate the mean. The number of antibody sequences (IGVH and IGVL) evaluated for each participant are n=68 (MOD1), n=45 (MOD2), n=117 (MOD3), n=123 (MOD4), n=110 (MOD6), n=109 (MOD7), n=144 (MOD8), n=102 (MOD9), n=132 (PFZ10), n=109 (MOD11), n=91 (PFZ12), n=78 (C001), n=66 (C003), and n=115 (C004). FIG. 9b shows distribution of the hydrophobicity GRAVY scores at the IGH CDR3 compared to a public database (see Methods for statistical analysis). The box limits are at the lower and upper quartiles, the center line indicates the median, the whiskers are 1.5× interquartile range, and the dots represent outliers. Statistical significance was determined using two-tailed Wilcoxon matched-pairs signed rank test (n.s.=non-significant, ****=p<0.0001).

FIGS. 10a, 10b, 10c, 10d, 10e, 10f, 10g, 10h, 10i, 10j, 10k and 10l are a set of diagrams showing the results of monoclonal antibody ELISAs. FIG. 10a is a graph showing antibody binding to SARS-CoV-2 RBD. ELISA $EC_{50}$ (half-maximal response) values for 84 antibodies isolated from Moderna vaccinees measured at 8 weeks after the boost and from convalescent individuals at 1.3 and 6.2 months. Horizontal bars indicate a geometric mean. Statistical significance was determined using a two-tailed Mann-Whitney U-test. Average of two or more experiments. FIGS. 10b-k are graphs showing ELISA titrations for antibodies in FIG. 10a. n=84 samples and isotype and control antibodies as indicated in the figure. FIG. 10l is a table showing a heat map summary of $EC_{50}$ values for binding to wild type RBD and the indicated mutants for 17 selected antibodies.

DETAILED DESCRIPTION OF THE INVENTION

Figure 5A:
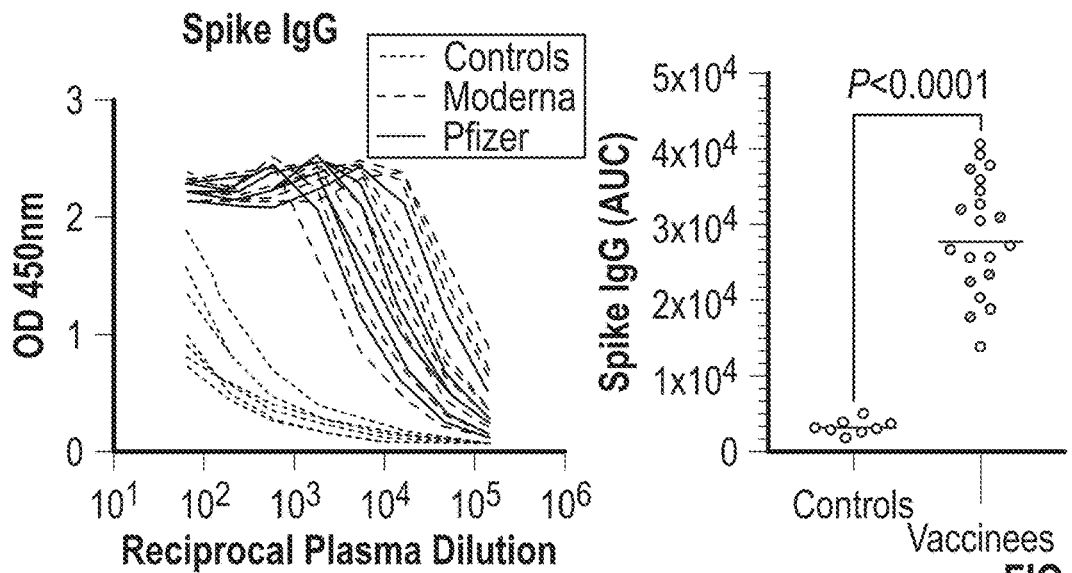
Figure 5B:
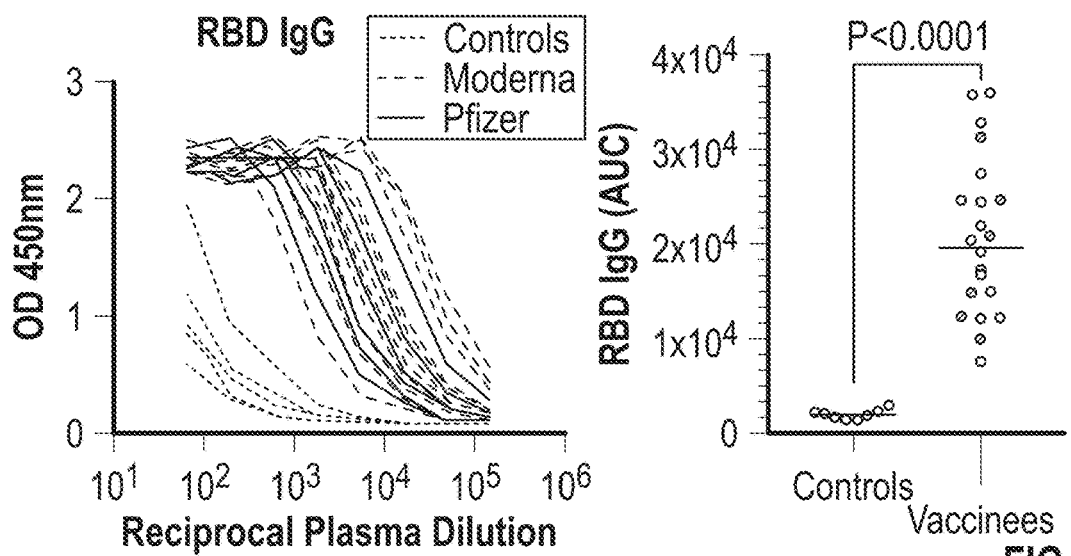
Figure 5C:
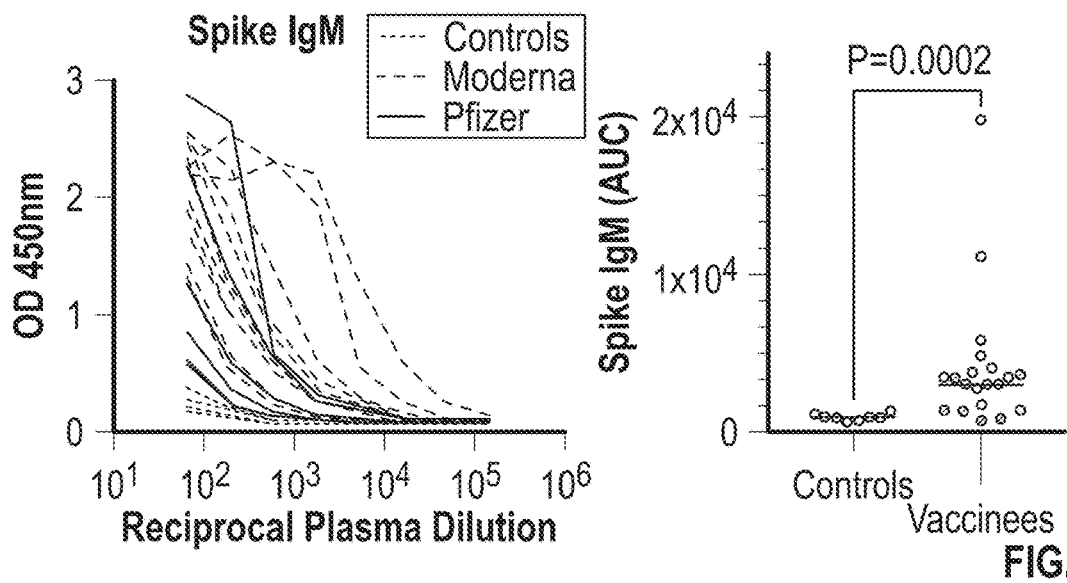
Figure 5D:
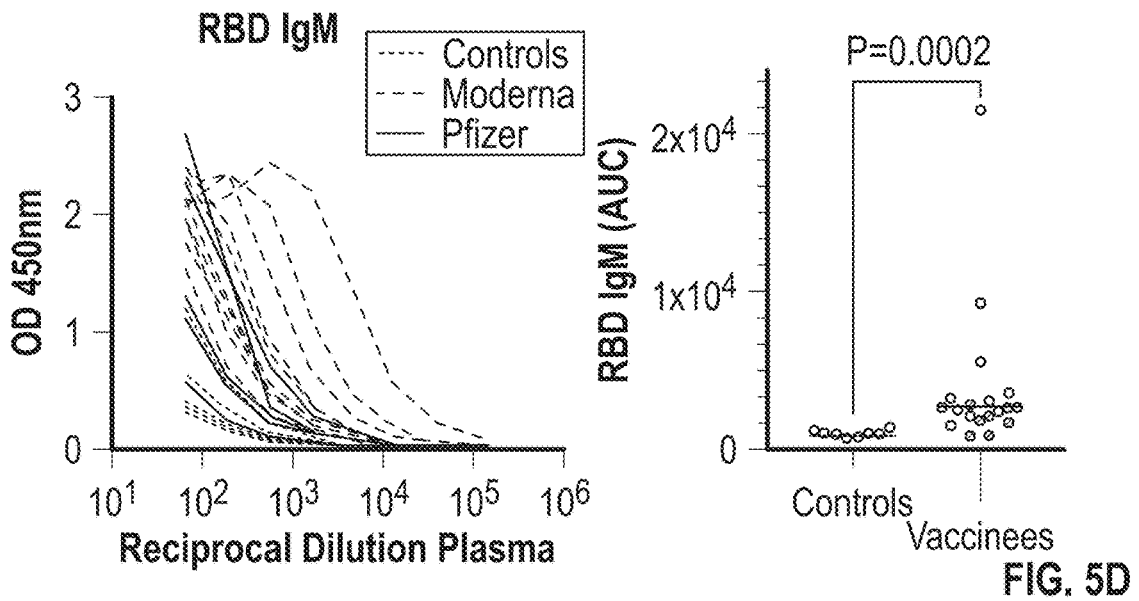
Figure 5E:
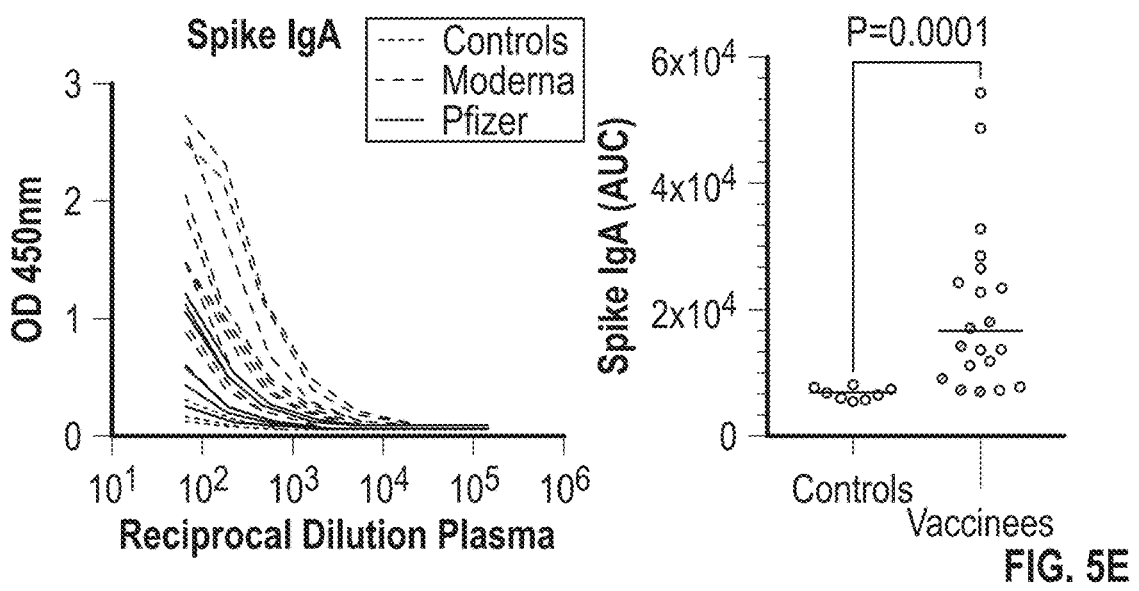
Figure 5F:
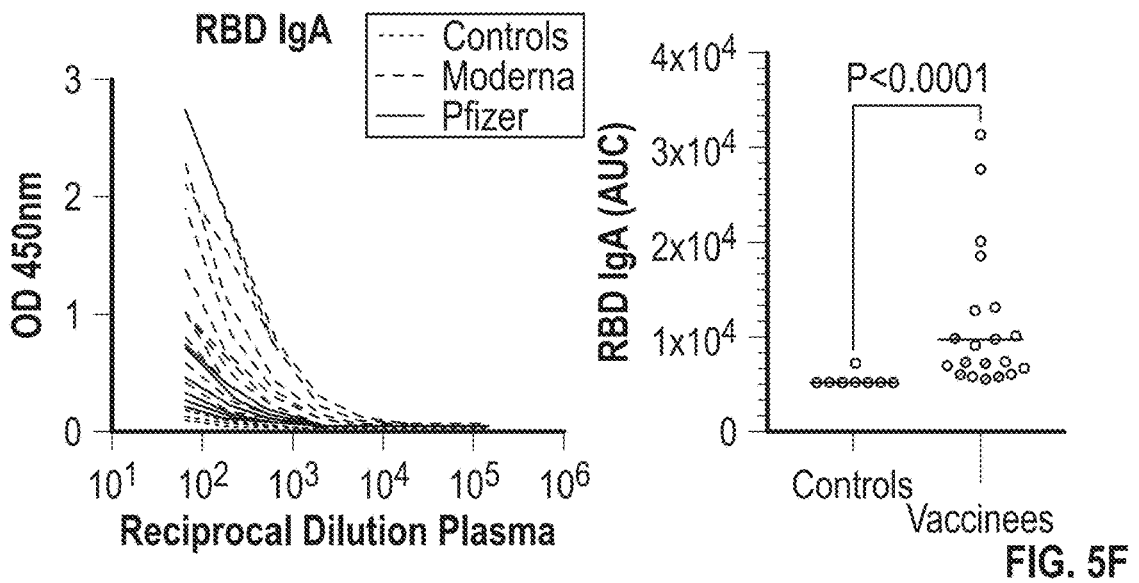

SARS-CoV-2 represents a serious public health concern. Methods to diagnose and treat persons who are infected with SARS-CoV-2 provide the opportunity to either prevent or control further spread of infection by SARS-CoV-2. These methods are especially important due to the ability of SARS-CoV-2 to infect persons through an airborne route.

This invention is based, at least in part, on unexpected neutralizing activities of the disclosed anti-SARS-CoV-2 antibodies or antigen-binding fragments thereof. These antibodies and antigen-binding fragments constitute a novel therapeutic strategy in protection from SARS-CoV-2 infections.

Neutralizing Anti-SARS-CoV-2 Antibodies
Antibodies

The invention disclosed herein involves neutralizing anti-SARS-CoV-2 antibodies or antigen-binding fragments thereof. These antibodies refer to a class of neutralizing antibodies that neutralize multiple SARS-CoV-2 virus strains. The antibodies are able to protect a subject prophylactically and therapeutically against a lethal challenge with a SARS-CoV-2 virus.

In one aspect, this disclosure provides an isolated anti-SARS-CoV-2 antibody or antigen-binding fragment thereof that binds specifically to a SARS-CoV-2 antigen. In some embodiments, the SARS-CoV-2 antigen comprises a portion of a Spike (S) polypeptide, such as a S polypeptide of a human or an animal SARS-CoV-2. In some embodiments, the SARS-CoV-2 antigen comprises the receptor-binding domain (RBD) of the S polypeptide. In some embodiments, the RBD comprises amino acids 319-541 of the S polypeptide. In some embodiments, the antibody or antigen-binding fragment thereof is capable of neutralizing a plurality of SARS-CoV-2 strains.

In some embodiments, the antibody or antigen-binding fragment thereof is capable of neutralizing a SARS-CoV-2 virus at an $IC_{50}$ concentration of less than 50 (e.g., 1, 5, 10, 20, 30, 40, 50) μg/ml.

The spike protein is important because it is present on the outside of intact SARS-CoV-2. Thus, it presents a target that can be used to inhibit or eliminate an intact virus before the virus has an opportunity to infect a cell. A representative amino acid sequence is provided below:

(Accession ID: NC_045512.2)
(SEQ ID NO: 357)
MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

-continued
IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPT

NGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

IGAEHVNNSYECDIPIGAGICASYQTQTNSPRRARSVASQSIIAYTMSLG

AENSVAYSNNSIAIPTNFTISVTTEILPVSMTKTSVDCTMYICGDSTECS

NLLLQYGSFCTQLNRALTGIAVEQDKNTQEVFAQVKQIYKTPPIKDFGGF

NFSQILPDPSKPSKRSFIEDLLFNKVTLADAGFIKQYGDCLGDIAARDLI

CAQKFNGLTVLPPLLTDEMIAQYTSALLAGTITSGWTFGAGAALQIPFAM

QMAYRFNGIGVTQNVLYENQKLIANQFNSAIGKIQDSLSSTASALGKLQD

VVNQNAQALNTLVKQLSSNFGAISSVLNDILSRLDKVEAEVQIDRLITGR

LQSLQTYVTQQLIRAAEIRASANLAATKMSECVLGQSKRVDFCGKGYHLM

SFPQSAPHGVVFLHVTYVPAQEKNFTTAPAICHDGKAHFPREGVFVSNGT

HWFVTQRNFYEPQIITTDNTFVSGNCDVVIGIVNNTVYDPLQPELDSFKE

ELDKYFKNHTSPDVDLGDISGINASVVNIQKEIDRLNEVAKNLNESLIDL

QELGKYEQYIKWPWYIWLGFIAGLIAIVMVTIMLCCMTSCCSCLKGCCSC

GSCCKFDEDDSEPVLKGVKLHYT

Listed below in Tables 2 and 4 are amino acid sequences of the heavy chain (HC) variable regions and light chain (LC) variable regions of exemplary antibodies.

In some embodiments, the antibody or antigen-binding fragment thereof comprises: three heavy chain complementarity determining regions (HCDRs) (HCDR1, HCDR2, and HCDR3) of a heavy chain variable region having the amino acid sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, or 167; and three light chain CDRs (LCDR1, LCDR2, and LCDR3) of a light chain variable region having the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168.

In some embodiments, the antibody or antigen-binding fragment thereof comprises: (i) a heavy chain variable region having an amino acid sequence with at least 75% identity to one selected from those in Table 2 or 4; and/or (ii) a light chain variable region having an amino acid sequence with at least 75% identity to one selected from those in Table 2 or 4.

In some embodiments, the antibody or antigen-binding fragment thereof comprises: (i) a heavy chain variable region having the amino acid sequence of one selected from those in Table 2 or 4; and/or (ii) a light chain variable region having the amino acid sequence of one selected from those in Table 2 or 4.

In some embodiments, the antibody or antigen-binding fragment thereof comprises a heavy chain variable region and a light chain variable region that comprises an amino acid sequence pair selected from those in Table 2 or 4.

In some embodiments, the antibody or antigen-binding fragment thereof comprises: a heavy chain variable region having an amino acid sequence with at least 75% identity to the amino acid sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, or 167; or having the amino acid sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, or 167; and a light chain variable region having an amino acid sequence with at least 75% identity to the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168; or having the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, or 168.

In some embodiments, the antibody or antigen-binding fragment thereof comprises a heavy chain variable region and a light chain variable region comprise the respective amino acid sequences of SEQ ID NOs: 1-2, 3-4, 5-6, 7-8, 9-10, 11-12, 13-14, 15-16, 17-18, 19-20, 21-22, 23-24, 25-26, 27-28, 29-30, 31-32, 33-34, 35-36, 37-38, 39-40, 41-42, 43-44, 45-46, 47-48, 49-50, 51-52, 53-54, 55-56, 57-58, 59-60, 61-62, 63-64, 65-66, 67-68, 69-70, 71-72, 73-74, 75-76, 77-78, 79-80, 81-82, 83-84, 85-86, 87-88, 89-90, 91-92, 93-94, 95-96, 97-98, 99-100, 101-102, 103-104, 105-106, 107-108, 109-110, 111-112, 113-114, 115-116, 117-118, 119-120, 121-122, 123-124, 125-126, 127-128, 129-130, 131-132, 133-134, 135-136, 137-138, 139-140, 141-142, 143-144, 145-146, 147-148, 149-150, 151-152, 153-154, 155-156, 157-158, 159-160, 161-162, 163-164, 165-166, or 167-168.

In some embodiments, the antibody or antigen-binding fragment thereof comprises (a) a first target binding site that specifically binds to an epitope within the S polypeptide, and (b) a second target binding site that binds to a different epitope on the S polypeptide or on a different molecule. In some embodiments, the multivalent antibody is a bivalent or bispecific antibody.

In some embodiments, the antibody or the antigen-binding fragment thereof further comprises a variant Fc constant region. In some embodiments, the antibody is a monoclonal antibody. In some embodiments, the antibody is a chimeric antibody, a humanized antibody, or a humanized monoclonal antibody. In some embodiments, the antibody is a single-chain antibody, Fab or Fab2 fragment.

In some embodiments, the antibody or the antigen-binding fragment thereof further comprises a variant Fc constant region. The antibody can be a monoclonal antibody. In some embodiments, the antibody can be a chimeric antibody, a humanized antibody, or a humanized monoclonal antibody. In some embodiments, the antibody can be a single-chain antibody, Fab or Fab2 fragment.

In some embodiments, the antibody or antigen-binding fragment thereof can be detectably labeled or conjugated to a toxin, a therapeutic agent, a polymer (e.g., polyethylene glycol (PEG)), a receptor, an enzyme, or a receptor ligand. For example, an antibody of the present invention may be coupled to a toxin (e.g., a tetanus toxin). Such antibodies may be used to treat animals, including humans, that are infected with the virus that is etiologically linked to SARS-CoV-2. The toxin-coupled antibody is thought to bind to a portion of a spike protein presented on an infected cell, and then kill the infected cell.

In another example, an antibody of the present invention may be coupled to a detectable tag. Such antibodies may be used within diagnostic assays to determine if an animal, such as a human, is infected with SARS-CoV-2. Examples of detectable tags include: fluorescent proteins (i.e., green fluorescent protein, red fluorescent protein, yellow fluorescent protein), fluorescent markers (i.e., fluorescein isothiocyanate, rhodamine, texas red), radiolabels (i.e., 3H, 32P, 125I), enzymes (i.e., β-galactosidase, horseradish peroxidase, β-glucuronidase, alkaline phosphatase), or an affinity tag (i.e., avidin, biotin, streptavidin). Methods to couple antibodies to a detectable tag are known in the art. Harlow et al., Antibodies: A Laboratory Manual, page 319 (Cold Spring Harbor Pub. 1988).

Fragment

In some embodiments, an antibody provided herein is an antibody fragment. Antibody fragments include, but are not limited to, Fab, Fab', Fab'-SH, F(ab')2, Fv, and single-chain Fv (scFv) fragments, and other fragments described below, e.g., diabodies, triabodies tetrabodies, and single-domain antibodies. For a review of certain antibody fragments, see Hudson et al., Nat. Med. 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869, 046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In some embodiments, a single-domain antibody is a human single-domain antibody (DOMANTIS, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

Chimeric and Humanized Antibodies

In some embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

Human Antibodies

In some embodiments, an antibody provided herein is a human antibody. Human antibodies can be produced using various techniques known in the art or using techniques described herein. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE technology; U.S. Pat. No. 5,770,429 describing HUMAB technology; U.S. Pat. No. 7,041,870 describing K-M MOUSE technology, and U.S. Patent Application Publication No. US 2007/0061900, describing VELOCI-MOUSE technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3): 927-937 (2005) and Vollmers and Brandlein, Methods and Findings in Experimental and Clinical Pharmacology, 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al., in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically displays antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., EMBO J, 12: 725-734 (1993). Finally, naive libraries can also be made synthetically by cloning unrearranged V-gene segments from stem cells and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example, U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360. Antibodies or antibody fragments isolated from human antibody libraries are considered human antibodies or human antibody fragments herein.

Variants

In some embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen binding.

Substitution, Insertion, and Deletion Variants

In some embodiments, antibody variants having one or more amino acid substitutions are provided. Sites of interest for substitutional mutagenesis include the HVRs and FRs. Conservative substitutions are defined herein. Amino acid substitutions may be introduced into an antibody of interest and the products screened for a desired activity, e.g., retained/improved antigen binding, decreased immunogenicity, or improved antibody-dependent cell-mediated cytotoxicity (ADCC) and complement-dependent cytotoxicity (CDC).

Accordingly, an antibody of the invention can comprise one or more conservative modifications of the CDRs, heavy chain variable region, or light variable regions described herein. A conservative modification or functional equivalent of a peptide, polypeptide, or protein disclosed in this invention refers to a polypeptide derivative of the peptide, polypeptide, or protein, e.g., a protein having one or more point mutations, insertions, deletions, truncations, a fusion protein, or a combination thereof. It substantially retains the activity to of the parent peptide, polypeptide, or protein (such as those disclosed in this invention). In general, a conservative modification or functional equivalent is at least 60% (e.g., any number between 60% and 100%, inclusive, e.g., 60%, 70%, 75%, 80%, 85%, 90%, 95%, 96%, 97%, 98%, and 99%) identical to a parent. Accordingly, within the scope of this invention are heavy chain variable region or light variable regions having one or more point mutations, insertions, deletions, truncations, a fusion protein, or a combination thereof, as well as antibodies having the variant regions.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) J. Mol. Biol. 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. (See www.ncbi.nlm.nih.gov).

As used herein, the term "conservative modifications" refers to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include: (i) amino acids with basic side chains (e.g., lysine, arginine, histidine), (ii) acidic side chains (e.g., aspartic acid, glutamic acid), (iii) uncharged polar side chains (e.g., glycine, asparagine, glutamine, serine, threonine, tyrosine, cysteine, tryptophan), (iv) nonpolar side chains (e.g., alanine, valine, leucine, isoleucine, proline, phenylalanine, methionine), (v) beta-branched side chains (e.g., threonine, valine, isoleucine), and (vi) aromatic side chains (e.g., tyrosine, phenylalanine, tryptophan, histidine). Non-conservative substitutions will entail exchanging a member of one of these classes for another class.

An exemplary substitutional variant is an affinity matured antibody, which may be conveniently generated, e.g., using phage display-based affinity maturation techniques such as those described in, e.g., Hoogenboom et al., in Methods in Molecular Biology 178:1-37 (O'Brien et al., ed., Human Press, Totowa, N.J., (2001). Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

Glycosylation Variants

In some embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites are created or removed.

For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Glycosylation of the constant region on N297 may be prevented by mutating the N297 residue to another residue, e.g., N297A, and/or by mutating an adjacent amino acid, e.g., 298 to thereby reduce glycosylation on N297.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies described herein to thereby produce an antibody with altered glycosylation. For example, EP 1,176,195 by Hanai et al. describes a cell line with a functionally disrupted FUT8 gene, which encodes a fucosyltransferase, such that antibodies expressed in such a cell line exhibit hypofucosylation. PCT Publication WO 03/035835 by Presta describes a variant Chinese Hamster Ovary cell line, Lcd 3 cells, with reduced ability to attach fucose to Asn(297)-linked carbohydrates, also resulting in hypofucosylation of antibodies expressed in that host cell (see also Shields, R. L. et al. (2002) J. Biol. Chem. 277:26733-26740). PCT Publication WO 99/54342 by Umana et al. describes cell lines engineered to express glycoprotein-modifying glycosyltransferases (e.g., beta(1,4)-N-acetylglucosaminyltransferase III (GnTIII)) such that antibodies expressed in the engineered cell lines exhibit increased bisecting GlcNac structures which result in increased ADCC activity of the antibodies (see also Umana et al. (1999) Nat. Biotech. 17: 176-180).

Ec Region Variants

The variable regions of the antibody described herein can be linked (e.g., covalently linked or fused) to an Fc, e.g., an IgG1, IgG2, IgG3 or IgG4 Fc, which may be of any allotype or isoallotype, e.g., for IgG1: Glm, Glm1(a), Glm2(x), Glm3(f), Glm17(z); for IgG2: G2m, G2m23(n); for IgG3: G3m, G3m21(g1), G3m28(g5), G3m11(b0), G3m5(b1), G3m13(b3), G3m14(b4), G3m10(b5), G3m15(s), G3m16(t), G3m6(c3), G3m24(c5), G3m26(u), G3m27(v); and for K: Km, Km1, Km2, Km3 (see, e.g., Jefferies et al. (2009) mAbs 1: 1). In some embodiments, the antibodies variable regions described herein are linked to an Fc that binds to one or more activating Fc receptors (FcγI, FcγIIa or FcγIIIa), and thereby stimulate ADCC and may cause T cell depletion. In some embodiments, the antibody variable regions described herein are linked to an Fc that causes depletion.

In some embodiments, the antibody variable regions described herein may be linked to an Fc comprising one or more modifications, typically to alter one or more functional properties of the antibody, such as serum half-life, complement fixation, Fc receptor binding, and/or antigen-dependent cellular cytotoxicity. Furthermore, an antibody described herein may be chemically modified (e.g., one or more chemical moieties can be attached to the antibody) or be modified to alter its glycosylation, to alter one or more functional properties of the antibody. The numbering of residues in the Fc region is that of the EU index of Kabat.

The Fc region encompasses domains derived from the constant region of an immunoglobulin, preferably a human immunoglobulin, including a fragment, analog, variant, mutant or derivative of the constant region. Suitable immunoglobulins include IgG1, IgG2, IgG3, IgG4, and other classes such as IgA, IgD, IgE and IgM. The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in combination. In some embodiments, an antibody of this invention has an Fc region other than that of a wild type IgA1. The antibody can have an Fc region from that of IgG (e.g., IgG1, IgG2, IgG3, and IgG4) or other classes such as IgA2, IgD, IgE, and IgM. The Fc can be a mutant form of IgA1.

The constant region of an immunoglobulin is responsible for many important antibody functions, including Fc receptor (FcR) binding and complement fixation. There are five major classes of heavy chain constant region, classified as IgA, IgG, IgD, IgE, IgM, each with characteristic effector functions designated by isotype. For example, IgG is separated into four subclasses known as IgG1, IgG2, IgG3, and IgG4.

Ig molecules interact with multiple classes of cellular receptors. For example, IgG molecules interact with three classes of Fcγ receptors (FcγR) specific for the IgG class of antibody, namely FcγRI, FcγRII, and FcγRIII. The important sequences for the binding of IgG to the FcγR receptors have been reported to be located in the CH2 and CH3 domains. The serum half-life of an antibody is influenced by the ability of that antibody to bind to an FcR.

In some embodiments, the Fc region is a variant Fc region, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity. For example, one may make modifications in the Fc region in order to generate an Fc variant that (a) has increased or decreased ADCC, (b) increased or decreased CDC, (c) has increased or decreased affinity for Clq and/or (d) has increased or decreased affinity for an Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc. substitutions therein, e.g., of the specific Fc region positions identified herein.

A variant Fc region may also comprise a sequence alteration wherein amino acids involved in disulfide bond formation are removed or replaced with other amino acids. Such removal may avoid reaction with other cysteine-containing proteins present in the host cell used to produce the antibodies described herein. Even when cysteine residues are removed, single chain Fc domains can still form a dimeric Fc domain that is held together non-covalently. In other embodiments, the Fc region may be modified to make it more compatible with a selected host cell. For example, one may remove the PA sequence near the N-terminus of a typical native Fc region, which may be recognized by a digestive enzyme in *E. coli* such as proline iminopeptidase. In other embodiments, one or more glycosylation sites within the Fc domain may be removed. Residues that are typically glycosylated (e.g., asparagine) may confer cytolytic response. Such residues may be deleted or substituted with unglycosylated residues (e.g., alanine). In other embodiments, sites involved in interaction with complement, such as the Clq binding site, may be removed from the Fc region. For example, one may delete or substitute the EKK sequence of human IgG1. In some embodiments, sites that affect binding to Fc receptors may be removed, preferably sites other than salvage receptor binding sites. In other embodiments, an Fc region may be modified to remove an ADCC site. ADCC sites are known in the art; see, for example, Molec. Immunol. 29 (5): 633-9 (1992) with regard to ADCC sites in IgG1. Specific examples of variant Fc domains are disclosed, for example, in WO 97/34631 and WO 96/32478.

In one embodiment, the hinge region of Fc is modified such that the number of cysteine residues in the hinge region is altered, e.g., increased or decreased. This approach is described further in U.S. Pat. No. 5,677,425 by Bodmer et al. The number of cysteine residues in the hinge region of Fc is altered to, for example, facilitate assembly of the light and heavy chains or to increase or decrease the stability of the antibody. In one embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the CI component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered Clq binding and/or reduced or abolished CDC. This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region may be modified to increase ADCC and/or to increase the affinity for an Fcγ receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439. Exemplary substitutions include 236A, 239D, 239E, 268D, 267E, 268E, 268F, 324T, 332D, and 332E. Exemplary variants include 239D/332E, 236A/332E, 236A/239D/332E, 268F/324T, 267E/268F, 267E/324T, and 267E/268F7324T. Other modifications for enhancing FcγR and complement interactions include but are not limited to substitutions 298A, 333A, 334A, 326A, 247I, 339D, 339Q, 280H, 290S, 298D, 298V, 243L, 292P, 300L, 396L, 305I, and 396L. These and other modifications are reviewed in Strohl, 2009, Current Opinion in Biotechnology 20:685-691.

Fc modifications that increase binding to an Fcγ receptor include amino acid modifications at any one or more of amino acid positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 324, 327, 329, 330, 335, 337, 3338, 340, 360, 373, 376, 379, 382, 388, 389, 398, 414, 416, 419, 430, 434, 435, 437, 438 or 439 of the Fc region, wherein the numbering of the residues in the Fc region is that of the EU index as in abat (WO00/42072).

Other Fc modifications that can be made to Fcs are those for reducing or ablating binding to FcγR and/or complement proteins, thereby reducing or ablating Fc-mediated effector functions such as ADCC, antibody-dependent cellular phagocytosis (ADCP), and CDC. Exemplary modifications include but are not limited substitutions, insertions, and deletions at positions 234, 235, 236, 237, 267, 269, 325, and 328, wherein numbering is according to the EU index. Exemplary substitutions include but are not limited to 234G, 235G, 236R, 237K, 267R, 269R, 325L, and 328R, wherein numbering is according to the EU index. An Fc variant may comprise 236R/328R. Other modifications for reducing FcγR and complement interactions include substitutions 297A, 234A, 235A, 237A, 318A, 228P, 236E, 268Q, 309L, 330S, 331S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, Current Opinion in Biotechnology 20:685-691.

Optionally, the Fc region may comprise a non-naturally occurring amino acid residue at additional and/or alternative positions known to one skilled in the art (see, e.g., U.S. Pat. Nos. 5,624,821; 6,277,375; 6,737,056; 6,194,551; 7,317,091; 8,101,720; WO00/42072; WO01/58957; WO02/06919; WO04/016750; WO04/029207; WO04/035752; WO04/074455; WO04/099249; WO04/063351; WO05/070963; WO05/040217, WO05/092925 and WO06/020114).

Fc variants that enhance affinity for an inhibitory receptor FcγRIIb may also be used. Such variants may provide an Fc fusion protein with immune-modulatory activities related to FcγRIIb cells, including, for example, B cells and monocytes. In one embodiment, the Fc variants provide selectively enhanced affinity to FcγRIIb relative to one or more activating receptors. Modifications for altering binding to FcγRIIb include one or more modifications at a position selected from the group consisting of 234, 235, 236, 237, 239, 266, 267, 268, 325, 326, 327, 328, and 332, according to the EU index. Exemplary substitutions for enhancing FcγRIIb affinity include but are not limited to 234D, 234E, 234F, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Exemplary substitutions include 235Y, 236D, 239D, 266M, 267E, 268D, 268E, 328F, 328W, and 328Y. Other Fc variants for enhancing binding to FcγRIIb include 235Y/267E, 236D/267E, 239D/268D, 239D/267E, 267E/268D, 267E/268E, and 267E/328F.

The affinities and binding properties of an Fc region for its ligand may be determined by a variety of in vitro assay methods (biochemical or immunological based assays) known in the art including but not limited to, equilibrium methods (e.g., ELISA, or radioimmunoassay), or kinetics (e.g., BIACORE analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

In some embodiments, the antibody is modified to increase its biological half-life. Various approaches are possible. For example, this may be done by increasing the binding affinity of the Fc region for FcRn. For example, one or more of the following residues can be mutated: 252, 254, 256, 433, 435, 436, as described in U.S. Pat. No. 6,277,375. Specific exemplary substitutions include one or more of the following: T252L, T254S, and/or T256F. Alternatively, to increase the biological half-life, the antibody can be altered within the CH1 or $C_L$ region to contain a salvage receptor binding epitope taken from two loops of a CH2 domain of an Fc region of an IgG, as described in U.S. Pat. Nos. 5,869,046 and 6,121,022 by Presta et al. Other exemplary variants that increase binding to FcRn and/or improve pharmacokinetic properties include substitutions at positions 259, 308, 428, and 434, including for example 259I, 308F, 428L, 428M, 434S, 434H, 434F, 434Y, and 434M. Other variants that increase Fc binding to FcRn include: 250E, 250Q, 428L, 428F, 250Q/428L (Hinton et al, 2004, J. Biol. Chem. 279(8): 6213-6216, Hinton et al. 2006 Journal of Immunology 176:346-356), 256A, 272A, 286A, 305A, 307A, 307Q, 311A, 312A, 376A, 378Q, 380A, 382A, 434A (Shields et al, Journal of Biological Chemistry, 2001, 276 (9):6591-6604), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, 308T/309P/311S (Dall Acqua et al. Journal of Immunology, 2002, 169:5171-5180, Dall'Acqua et al., 2006, Journal of Biological Chemistry 281:23514-23524). Other modifications for modulating FcRn binding are described in Yeung et al., 2010, J Immunol, 182:7663-7671. In some embodiments, hybrid IgG isotypes with particular biological characteristics may be used. For example, an IgG1/IgG3 hybrid variant may be constructed by substituting IgG 1 positions in the CH2 and/or CH3 region with the amino acids from IgG3 at positions where the two isotypes differ. Thus a hybrid variant IgG antibody may be constructed that comprises one or more substitutions, e.g., 274Q, 276K, 300F, 339T, 356E, 358M, 384S, 392N, 397M, 422I, 435R, and 436F. In other embodiments described herein, an IgG1/IgG2 hybrid variant may be constructed by substituting IgG2 positions in the CH2 and/or CH3 region with amino acids from IgG1 at positions where the two isotypes differ. Thus a hybrid variant IgG antibody may be constructed chat comprises one or more substitutions, e.g., one or more of the following amino acid substitutions: 233E, 234L, 235L, 236G (referring to an insertion of a glycine at position 236), and 321 h.

Moreover, the binding sites on human IgG1 for FcγRI, FcγRII, FcγRIII, and FcRn have been mapped and variants with improved binding have been described (see Shields, R. L. et al. (2001) J. Biol. Chem. 276:6591-6604). Specific mutations at positions 256, 290, 298, 333, 334, and 339 were shown to improve binding to FcγRIII. Additionally, the following combination mutants were shown to improve FcγRIII binding: T256A/S298A, S298A/E333A, S298A/K224A, and S298A/E333A/K334A, which has been shown to exhibit enhanced FcγRIIIa binding and ADCC activity (Shields et al., 2001). Other IgG1 variants with strongly enhanced binding to FcγRIIIa have been identified, including variants with S239D/I332E and S239D/I332E/A330L mutations which showed the greatest increase in affinity for FcγRIIIa, a decrease in FcγRIIb binding, and strong cytotoxic activity in cynomolgus monkeys (Lazar et al., 2006). Introduction of the triple mutations into antibodies such as alemtuzumab (CD52-specific), trastuzumab (HER2/neu-specific), rituximab (CD20-specific), and cetuximab (EGFR-specific) translated into greatly enhanced ADCC activity in vitro, and the S239D/I332E variant showed an enhanced capacity to deplete B cells in monkeys (Lazar et al., 2006). In addition, IgG1 mutants containing L235V, F243L, R292P, Y300L and P396L mutations which exhibited enhanced binding to FcγRIIIa and concomitantly enhanced ADCC activity in transgenic mice expressing human FcγRIIIa in models of B cell malignancies and breast cancer have been identified (Stavenhagen et al., 2007; Nordstrom et al., 2011). Other Fc mutants that may be used include: S298A/E333A/L334A, S239D/I332E, S239D/I332E/A330L, L235V/F243L/R292P/Y300L/P396L, and M428L/N434S.

In some embodiments, an Fc is chosen that has reduced binding to FcγRs. An exemplary Fc, e.g., IgG1 Fc, with reduced FcγR binding, comprises the following three amino acid substitutions: L234A, L235E, and G237A.

In some embodiments, an Fc is chosen that has reduced complement fixation. An exemplary Fc, e.g., IgG1 Fc, with reduced complement fixation, has the following two amino acid substitutions: A330S and P331S.

In some embodiments, an Fc is chosen that has essentially no effector function, i.e., it has reduced binding to FcγRs and reduced complement fixation. An exemplary Fc, e.g., IgG1 Fc, that is effectorless, comprises the following five mutations: L234A, L235E, G237A, A330S, and P331S.

When using an IgG4 constant domain, it is usually preferable to include the substitution S228P, which mimics the hinge sequence in IgG1 and thereby stabilizes IgG4 molecules.

Multivalent Antibodies

In one embodiment, the antibodies of the invention may be monovalent or multivalent (e.g., bivalent, trivalent, etc.). As used herein, the term "valency" refers to the number of potential target binding sites associated with an antibody. Each target binding site specifically binds one target molecule or specific position or locus on a target molecule. When an antibody is monovalent, each binding site of the molecule will specifically bind to a single antigen position or epitope. When an antibody comprises more than one target binding site (multivalent), each target binding site may specifically bind the same or different molecules (e.g., may bind to different ligands or different antigens, or different epitopes or positions on the same antigen). See, for example, U.S.P.N. 2009/0130105. In each case, at least one of the binding sites will comprise an epitope, motif or domain associated with a DLL3 isoform.

In one embodiment, the antibodies are bispecific antibodies in which the two chains have different specificities, as described in Millstein et al., 1983, Nature, 305:537-539. Other embodiments include antibodies with additional specificities, such as trispecific antibodies. Other more sophisticated compatible multispecific constructs and methods of their fabrication are set forth in U.S.P.N. 2009/0155255, as well as WO 94/04690; Suresh et al., 1986, Methods in Enzymology, 121:210; and WO96/27011.

As stated above, multivalent antibodies may immunospecifically bind to different epitopes of the desired target molecule or may immunospecifically bind to both the target molecule as well as a heterologous epitope, such as a heterologous polypeptide or solid support material. In some embodiments, the multivalent antibodies may include bispecific antibodies or trispecific antibodies. Bispecific antibodies also include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art and are disclosed in U.S. Pat. No. 4,676,980, along with a number of cross-linking techniques.

In some embodiments, antibody variable domains with the desired binding specificities (antibody-antigen combining sites) are fused to immunoglobulin constant domain sequences, such as an immunoglobulin heavy chain constant domain comprising at least part of the hinge, CH2, and/or CH3 regions, using methods well known to those of ordinary skill in the art.

Antibody Derivatives

An antibody provided herein may be further modified to contain additional nonproteinaceous moieties that are known in the art and readily available. The moieties suitable for derivatization of the antibody include but are not limited to water-soluble polymers.

Non-limiting examples of water-soluble polymers include, but are not limited to, PEG, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Another modification of the antibodies described herein is pegylation. An antibody can be pegylated to, for example, increase the biological (e.g., serum) half-life of the antibody. To pegylate an antibody, the antibody, or fragment thereof, typically is reacted with PEG, such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (CI-CIO) alkoxy- or aryloxy-polyethylene glycol or polyethylene glycol-maleimide. In some embodiments, the antibody to be pegylated is an aglycosylated antibody. Methods for pegylating proteins are known in the art and can be applied to the antibodies described herein. See, for example, EP 0 154 316 by Nishimura et al. and EP0401384 by Ishikawa et al.

The present invention also encompasses a human monoclonal antibody described herein conjugated to a therapeutic agent, a polymer, a detectable label or enzyme. In one embodiment, the therapeutic agent is a cytotoxic agent. In one embodiment, the polymer is PEG.

Nucleic Acids, Expression Cassettes, and Vectors

The present invention provides isolated nucleic acid segments that encode the polypeptides, peptide fragments, and coupled proteins of the invention. The nucleic acid segments of the invention also include segments that encode for the same amino acids due to the degeneracy of the genetic code. For example, the amino acid threonine is encoded by ACU, ACC, ACA, and ACG and is therefore degenerate. It is intended that the invention includes all variations of the polynucleotide segments that encode for the same amino acids. Such mutations are known in the art (Watson et al., Molecular Biology of the Gene, Benjamin Cummings 1987). Mutations also include alteration of a nucleic acid segment to encode for conservative amino acid changes, for example, the substitution of leucine for isoleucine and so forth. Such mutations are also known in the art. Thus, the genes and nucleotide sequences of the invention include both the naturally occurring sequences as well as mutant forms.

The nucleic acid segments of the invention may be contained within a vector. A vector may include, but is not limited to, any plasmid, phagemid, F-factor, virus, cosmid, or phage in a double- or single-stranded linear or circular form which may or may not be self transmissible or mobilizable. The vector can also transform a prokaryotic or eukaryotic host either by integration into the cellular genome or exist extra-chromosomally (e.g., autonomous replicating plasmid with an origin of replication).

Preferably the nucleic acid segment in the vector is under the control of, and operably linked to, an appropriate promoter or other regulatory elements for transcription in vitro or in a host cell, such as a eukaryotic cell, or a microbe, e.g., bacteria. The vector may be a shuttle vector that functions in multiple hosts. The vector may also be a cloning vector that typically contains one or a small number of restriction endonuclease recognition sites at which foreign DNA sequences can be inserted in a determinable fashion. Such insertion can occur without loss of essential biological function of the cloning vector. A cloning vector may also contain a marker gene that is suitable for use in the identification and selection of cells transformed with the cloning vector. Examples of marker genes are tetracycline resistance or ampicillin resistance. Many cloning vectors are commercially available (Stratagene, New England Biolabs, Clonetech).

The nucleic acid segments of the invention may also be inserted into an expression vector. Typically an expression vector contains prokaryotic DNA elements coding for a bacterial replication origin and an antibiotic resistance gene to provide for the amplification and selection of the expression vector in a bacterial host; regulatory elements that control initiation of transcription such as a promoter; and DNA elements that control the processing of transcripts such as introns, or a transcription termination/polyadenylation sequence.

Methods to introduce nucleic acid segment into a vector are available in the art (Sambrook et al., Molecular Cloning: A Laboratory Manual, 3rd edition, Cold Spring Harbor Press, Cold Spring Harbor, N.Y. (2001)). Briefly, a vector into which a nucleic acid segment is to be inserted is treated with one or more restriction enzymes (restriction endonuclease) to produce a linearized vector having a blunt end, a "sticky" end with a 5' or a 3' overhang, or any combination of the above. The vector may also be treated with a restriction enzyme and subsequently treated with another modifying enzyme, such as a polymerase, an exonuclease, a phosphatase or a kinase, to create a linearized vector that has characteristics useful for ligation of a nucleic acid segment into the vector. The nucleic acid segment that is to be inserted into the vector is treated with one or more restriction enzymes to create a linearized segment having a blunt end, a "sticky" end with a 5' or a 3' overhang, or any combination of the above. The nucleic acid segment may also be treated with a restriction enzyme and subsequently treated with another DNA modifying enzyme. Such DNA modifying enzymes include, but are not limited to, polymerase, exonuclease, phosphatase or a kinase, to create a nucleic acid segment that has characteristics useful for ligation of a nucleic acid segment into the vector.

The treated vector and nucleic acid segment are then ligated together to form a construct containing a nucleic acid segment according to methods available in the art (Sambrook et al., Molecular Cloning: A Laboratory Manual, 3rd edition, Cold Spring Harbor Press, Cold Spring Harbor, N.Y. (2001)). Briefly, the treated nucleic acid fragment, and the treated vector are combined in the presence of a suitable buffer and ligase. The mixture is then incubated under appropriate conditions to allow the ligase to ligate the nucleic acid fragment into the vector.

The invention also provides an expression cassette which contains a nucleic acid sequence capable of directing expression of a particular nucleic acid segment of the invention, either in vitro or in a host cell. Also, a nucleic acid segment of the invention may be inserted into the expression cassette such that an anti-sense message is produced. The expression cassette is an isolatable unit such that the expression cassette may be in linear form and functional for in vitro transcription and translation assays. The materials and procedures to conduct these assays are commercially available from Promega Corp. (Madison, Wis.). For example, an in vitro transcript may be produced by placing a nucleic acid sequence under the control of a T7 promoter and then using T7 RNA polymerase to produce an in vitro transcript. This transcript may then be translated in vitro through use of a rabbit reticulocyte lysate. Alternatively, the expression cassette can be incorporated into a vector allowing for replication and amplification of the expression cassette within a host cell or also in vitro transcription and translation of a nucleic acid segment.

Such an expression cassette may contain one or a plurality of restriction sites allowing for placement of the nucleic acid segment under the regulation of a regulatory sequence. The expression cassette can also contain a termination signal operably linked to the nucleic acid segment as well as regulatory sequences required for proper translation of the nucleic acid segment. The expression cassette containing the nucleic acid segment may be chimeric, meaning that at least one of its components is heterologous with respect to at least one of its other components. The expression cassette may also be one that is naturally occurring but has been obtained in a recombinant form useful for heterologous expression. Expression of the nucleic acid segment in the expression cassette may be under the control of a constitutive promoter or an inducible promoter, which initiates transcription only when the host cell is exposed to some particular external stimulus.

The expression cassette may include in the 5'-3' direction of transcription, a transcriptional and translational initiation region, a nucleic acid segment and a transcriptional and translational termination region functional in vivo and/or in vitro. The termination region may be native with the transcriptional initiation region, may be native with the nucleic acid segment, or may be derived from another source.

The regulatory sequence can be a polynucleotide sequence located upstream (5' non-coding sequences), within, or downstream (3' non-coding sequences) of a coding sequence, and which influences the transcription, RNA processing or stability, or translation of the associated coding sequence. Regulatory sequences can include, but are not limited to, enhancers, promoters, repressor binding sites, translation leader sequences, introns, and polyadenylation signal sequences. They may include natural and synthetic sequences as well as sequences, which may be a combination of synthetic and natural sequences. While regulatory sequences are not limited to promoters, some useful regulatory sequences include constitutive promoters, inducible promoters, regulated promoters, tissue-specific promoters, viral promoters, and synthetic promoters.

A promoter is a nucleotide sequence that controls the expression of the coding sequence by providing the recognition for RNA polymerase and other factors required for proper transcription. A promoter includes a minimal promoter, consisting only of all basal elements needed for transcription initiation, such as a TATA-box and/or initiator that is a short DNA sequence comprised of a TATA-box and other sequences that serve to specify the site of transcription initiation, to which regulatory elements are added for control of expression. A promoter may be derived entirely from a native gene, or be composed of different elements derived from different promoters found in nature, or even be comprised of synthetic DNA segments. A promoter may contain DNA sequences that are involved in the binding of protein factors that control the effectiveness of transcription initiation in response to physiological or developmental conditions.

The invention also provides a construct containing a vector and an expression cassette. The vector may be selected from, but not limited to, any vector previously described. Into this vector may be inserted an expression cassette through methods known in the art and previously described (Sambrook et al., Molecular Cloning: A Laboratory Manual, 3rd edition, Cold Spring Harbor Press, Cold Spring Harbor, N.Y. (2001)). In one embodiment, the regulatory sequences of the expression cassette may be derived from a source other than the vector into which the expression cassette is inserted. In another embodiment, a construct containing a vector and an expression cassette is formed upon insertion of a nucleic acid segment of the invention into a vector that itself contains regulatory sequences. Thus, an expression cassette is formed upon insertion of the nucleic acid segment into the vector. Vectors containing regulatory sequences are available commercially, and methods for their use are known in the art (Clonetech, Promega, Stratagene).

In another aspect, this disclosure also provides (i) a nucleic acid molecule encoding a polypeptide chain of the antibody or antigen-binding fragment thereof described above; (ii) a vector comprising the nucleic acid molecule as described; and (iii) a cultured host cell comprising the vector as described. Also provided is a method for producing a polypeptide, comprising: (a) obtaining the cultured host cell as described; (b) culturing the cultured host cell in a medium under conditions permitting expression of a polypeptide encoded by the vector and assembling of an antibody or fragment thereof; and (c) purifying the antibody or fragment from the cultured cell or the medium of the cell.

Methods of Production

Antibodies may be produced using recombinant methods and compositions, e.g., as described in U.S. Pat. No. 4,816,567. In one embodiment, an isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g., a Chinese Hamster Ovary (CHO) cell or lymphoid cell (e.g., Y0, NS0, Sp20 cell). In one embodiment, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, a nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified, which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include CHO cells, including DHFR-CHO cells (Urlaub et al., Proc. Natl. Acad. Sci. USA 77:4216 (1980)); and myeloma cell lines such as Y0, NS0, and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Compositions and Kits

The antibodies of this invention represent an excellent way for the development of antiviral therapies either alone or in antibody cocktails with additional anti-SARS-CoV-2 virus antibodies for the treatment of human SARS-CoV-2 infections in humans.

In another aspect, the present invention provides a pharmaceutical composition comprising the antibodies of the present invention described herein formulated together with a pharmaceutically acceptable carrier. The composition may optionally contain one or more additional pharmaceutically active ingredients, such as another antibody or a therapeutic agent.

In some embodiments, the pharmaceutical comprises two or more of the antibody or antigen-binding fragment thereof described above, such as any combinations of the antibody or antigen-binding fragment thereof comprising a heavy chain and a light chain that comprise the respective amino acid sequences described herein.

The pharmaceutical compositions of the invention also can be administered in a combination therapy with, for example, another immune-stimulatory agent, an antiviral agent, or a vaccine, etc. In some embodiments, a composition comprises an antibody of this invention at a concentration of at least 1 mg/ml, 5 mg/ml, 10 mg/ml, 50 mg/ml, 100 mg/ml, 150 mg/ml, 200 mg/ml, 1-300 mg/ml, or 100-300 mg/ml.

In some embodiments, the second therapeutic agent comprises an anti-inflammatory drug or an antiviral compound. In some embodiments, the antiviral compound comprises: a nucleoside analog, a peptoid, an oligopeptide, a polypeptide, a protease inhibitor, a 3C-like protease inhibitor, a papain-like protease inhibitor, or an inhibitor of an RNA dependent RNA polymerase. In some embodiments, the antiviral compound may include: acyclovir, gancyclovir, vidarabine, foscarnet, cidofovir, amantadine, ribavirin, trifluorothymidine, zidovudine, didanosine, zalcitabine or an interferon. In some embodiments, the interferon is an interferon-α or an interferon-β.

Also within the scope of this disclosure is use of the pharmaceutical composition in the preparation of a medicament for the diagnosis, prophylaxis, treatment, or combination thereof of a condition resulting from a SARS-CoV-2.

The pharmaceutical composition can comprise any number of excipients. Excipients that can be used include carriers, surface-active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: The Science and Practice of Pharmacy, 20th Ed. (Lippincott Williams & Wilkins 2003), the disclosure of which is incorporated herein by reference.

Preferably, a pharmaceutical composition is suitable for intravenous, intramuscular, subcutaneous, parenteral, spinal or epidermal administration (e.g., by injection or infusion). Depending on the route of administration, the active compound can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the present invention described herein can be administered via a non-parenteral route, such as a topical, epidermal or mucosal route of administration, e.g., intranasally, orally, vaginally, rectally, sublingually or topically.

The pharmaceutical compositions of the invention may be prepared in many forms that include tablets, hard or soft gelatin capsules, aqueous solutions, suspensions, and liposomes and other slow-release formulations, such as shaped polymeric gels. An oral dosage form may be formulated such that the antibody is released into the intestine after passing through the stomach. Such formulations are described in U.S. Pat. No. 6,306,434 and in the references contained therein.

Oral liquid pharmaceutical compositions may be in the form of, for example, aqueous or oily suspensions, solutions, emulsions, syrups or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives.

An antibody can be formulated for parenteral administration (e.g., by injection, for example, bolus injection or continuous infusion) and may be presented in unit dosage form in ampules, prefilled syringes, small volume infusion containers or multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Pharmaceutical compositions suitable for rectal administration can be prepared as unit dose suppositories. Suitable carriers include saline solution and other materials commonly used in the art.

For administration by inhalation, an antibody can be conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, an antibody may take the form of a dry powder composition, for example, a powder mix of a modulator and a suitable powder base such as lactose or starch. The powder composition may be presented in unit dosage form in, for example, capsules or cartridges or, e.g., gelatin or blister packs from which the powder may be administered with the aid of an inhalator or insufflator. For intra-nasal administration, an antibody may be administered via a liquid spray, such as via a plastic bottle atomizer.

Pharmaceutical compositions of the invention may also contain other ingredients such as flavorings, colorings, antimicrobial agents, or preservatives. It will be appreciated that the amount of an antibody required for use in treatment will vary not only with the particular carrier selected but also with the route of administration, the nature of the condition being treated and the age and condition of the patient. Ultimately the attendant health care provider may determine proper dosage. In addition, a pharmaceutical composition may be formulated as a single unit dosage form.

The pharmaceutical composition of the present invention can be in the form of sterile aqueous solutions or dispersions. It can also be formulated in a microemulsion, liposome, or other ordered structure suitable to high drug concentration.

An antibody of the present invention described herein can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably, until the patient shows partial or complete amelioration of symptoms of disease. Thereafter, the patient can be administered a prophylactic regime.

The amount of active ingredient that can be combined with a carrier material to produce a single dosage form will vary depending upon the subject being treated and the particular mode of administration and will generally be that amount of the composition, which produces a therapeutic effect. Generally, out of one hundred percent, this amount will range from about 0.01% to about 99% of active ingredient, preferably from about 0.1% to about 70%, most preferably from about 1% to about 30% of active ingredient in combination with a pharmaceutically acceptable carrier.

Dosage regimens can be adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, the antibody can be administered as a sustained release formulation, in which case less frequent administration is required. For administration of the antibody, the dosage ranges from about 0.0001 to 800 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/ml and in some methods about 25-300 µg/ml. A "therapeutically effective dosage" of an antibody of the invention preferably results in a decrease in severity of disease symptoms, an increase in frequency and duration of disease symptom-free periods, or a prevention of impairment or disability due to the disease affliction. For example, for the treatment of SARS-CoV-2 infection in a subject, a "therapeutically effective dosage" preferably inhibits SARS-CoV-2 virus replication or uptake by host cells by at least about 20%, more preferably by at least about 40%, even more preferably by at least about 60%, and still more preferably by at least about 80% relative to untreated subjects. A therapeutically effective amount of a therapeutic compound can neutralize SARS-CoV-2 virus, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In some embodiments, the human monoclonal antibodies of the invention described herein can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs. See, e.g., U.S. Pat. Nos. 4,522,811; 5,374,548; 5,416,016; and 5,399,331; V. V. Ranade (1989) Clin. Pharmacol. 29:685; Umezawa et al., (1988) Biochem. Biophys. Res. Commun. 153:1038; Bloeman et al. (1995) FEBS Lett. 357:140; M. Owais et al. (1995) Antimicrob. Agents Chemother. 39:180; Briscoe et al. (1995) Am. Physiol. 1233:134; Schreier et al. (1994). Biol. Chem. 269:9090; Keinanen and Laukkanen (1994) FEBS Lett. 346:123; and Killion and Fidler (1994) Immunomethods 4:273.

In some embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor-mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can also be delivered in a vesicle, in particular, a liposome (see, for example, Langer (1990) Science 249: 1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389), incorporated herein by reference. Nanoparticles may be developed and conjugated to antibodies contained in pharmaceutical compositions to target cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.) and the HUMIRA™ Pen (Abbott Labs, Abbott Park, IL), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 300 mg and in about 10 to about 300 mg for the other dosage forms.

In another aspect, this disclosure provides a kit comprising a pharmaceutically acceptable dose unit of the antibody or antigen-binding fragment thereof or of the pharmaceutical composition as described above. Also within the scope of this disclosure is a kit for the diagnosis, prognosis or monitoring of treatment of SARS-CoV-2 in a subject, comprising: the antibody or antigen-binding fragment thereof as described; and a least one detection reagent that binds specifically to the antibody or antigen-binding fragment thereof.

In some embodiments, the kit also includes a container that contains the composition and optionally informational material. The informational material can be descriptive, instructional, marketing or other material that relates to the methods described herein and/or the use of the agents for therapeutic benefit. In an embodiment, the kit also includes an additional therapeutic agent, as described above. For example, the kit includes a first container that contains the composition and a second container for the additional therapeutic agent.

The informational material of the kits is not limited in its form. In some embodiments, the informational material can include information about production of the composition, concentration, date of expiration, batch or production site information, and so forth. In one embodiment, the informational material relates to methods of administering the composition, e.g., in a suitable dose, dosage form, or mode of administration (e.g., a dose, dosage form, or mode of administration described herein), to treat a subject in need thereof. In one embodiment, the instructions provide a dosing regimen, dosing schedule, and/or route of administration of the composition or the additional therapeutic agent. The information can be provided in a variety of formats, including printed text, computer-readable material, video recording, or audio recording, or information that contains a link or address to substantive material.

The kit can include one or more containers for the composition. In some embodiments, the kit contains separate containers, dividers, or compartments for the composition and informational material. For example, the composition can be contained in a bottle or vial, and the informational material can be contained in a plastic sleeve or packet. In other embodiments, the separate elements of the kit are contained within a single, undivided container. For example, the composition is contained in a bottle or vial that has attached thereto the informational material in the form of a label. In some embodiments, the kit includes a plurality (e.g., a pack) of individual containers, each containing one or more unit dosage forms (e.g., a dosage form described herein) of the agents.

The kit optionally includes a device suitable for administration of the composition or other suitable delivery device. The device can be provided pre-loaded with one or both of the agents or can be empty, but suitable for loading. Such a kit may optionally contain a syringe to allow for injection of the antibody contained within the kit into an animal, such as a human.

Methods of Use
Methods of Treatment

The antibodies, compositions, and formulations described herein can be used to neutralize SARS-CoV-2 virus and thereby treating or preventing SARS-CoV-2 infections.

Accordingly, in one aspect, this disclosure further provides a method of neutralizing SARS-CoV-2 in a subject, comprising administering to a subject in need thereof a therapeutically effective amount of the antibody or antigen-binding fragment thereof or a therapeutically effective amount of the pharmaceutical composition, as described above.

In another aspect, this disclosure additionally provides a method of preventing or treating a SARS-CoV-2 infection, comprising administering to a subject in need thereof a therapeutically effective amount of the antibody or antigen-binding fragment thereof or a therapeutically effective amount of the pharmaceutical composition, as described above.

The neutralizing of the SARS-CoV-2 virus can be done via (i) inhibiting SARS-CoV-2 virus binding to a target cell; (ii) inhibiting SARS-CoV-2 virus uptake by a target cell; (iii) inhibiting SARS-CoV-2 virus replication; and (iv) inhibiting SARS-CoV-2 virus particles release from infected cells. One skilled in the art possesses the ability to perform any assay to assess neutralization of SARS-CoV-2 virus.

Notably, the neutralizing properties of antibodies may be assessed by a variety of tests, which all may assess the consequences of (i) inhibition of SARS-CoV-2 virus binding to a target cell; (ii) inhibition of SARS-CoV-2 virus uptake by a target cell; (iii) inhibition of SARS-CoV-2 virus replication; and (iv) inhibition of SARS-CoV-2 virus particles release from infected cells. In other words, implementing different tests may lead to the observation of the same consequence, i.e., the loss of infectivity of the SARS-CoV-2 virus. Thus, in one embodiment, the present invention provides a method of neutralizing SARS-CoV-2 virus in a subject comprising administering to the subject a therapeutically effective amount of the antibody of the present invention described herein.

Another aspect of the present invention provides a method of treating a SARS-CoV-2-related disease. Such a method includes therapeutic (following SARS-CoV-2 infection) and prophylactic (prior to SARS-CoV-2 exposure, infection, or pathology). For example, therapeutic and prophylactic methods of treating an individual for a SARS-CoV-2 infection include treatment of an individual having or at risk of having a SARS-CoV-2 infection or pathology, treating an individual with a SARS-CoV-2 infection, and methods of protecting an individual from a SARS-CoV-2 infection, to decrease or reduce the probability of a SARS-CoV-2 infection in an individual, to decrease or reduce susceptibility of an individual to a SARS-CoV-2 infection, or to inhibit or prevent a SARS-CoV-2 infection in an individual, and to decrease, reduce, inhibit or suppress transmission of a SARS-CoV-2 from an infected individual to an uninfected individual. Such methods include administering an antibody of the present invention or a composition comprising the antibody disclosed herein to therapeutically or prophylactically treat (vaccinate or immunize) an individual having or at risk of having a SARS-CoV-2 infection or pathology. Accordingly, methods can treat the SARS-CoV-2 infection or pathology, or provide the individual with protection from infection (e.g., prophylactic protection).

In one embodiment, a method of treating a SARS-CoV-2-related disease comprises administering to an individual in need thereof an antibody or therapeutic composition disclosed herein in an amount sufficient to reduce one or more physiological conditions or symptoms associated with a SARS-CoV-2 infection or pathology, thereby treating the SARS-CoV-2-related disease.

In one embodiment, an antibody or therapeutic composition disclosed herein is used to treat a SARS-CoV-2-related disease. Use of an antibody or therapeutic composition disclosed herein treats a SARS-CoV-2-related disease by reducing one or more physiological conditions or symptoms associated with a SARS-CoV-2 infection or pathology. In aspects of this embodiment, administration of an antibody or therapeutic composition disclosed herein is in an amount sufficient to reduce one or more physiological conditions or symptoms associated with a SARS-CoV-2 infection or pathology, thereby treating the SARS-CoV-2-based disease. In other aspects of this embodiment, administration of an antibody or therapeutic composition disclosed herein is in an amount sufficient to increase, induce, enhance, augment, promote or stimulate SARS-CoV-2 clearance or removal; or decrease, reduce, inhibit, suppress, prevent, control, or limit transmission of SARS-CoV-2 to another individual.

One or more physiological conditions or symptoms associated with a SARS-CoV-2 infection or pathology will respond to a method of treatment disclosed herein. The symptoms of SARS-CoV-2 infection or pathology vary, depending on the phase of infection.

In some embodiments, the method of neutralizing SARS-CoV-2 in a subject comprises administering to a subject in need thereof a therapeutically effective amount of a first antibody or antigen-binding fragment thereof and a second antibody or antigen-binding fragment thereof of the antibody or antigen-binding fragment, as described above, wherein the first antibody or antigen-binding fragment thereof and the second antibody or antigen binding fragment thereof exhibit synergistic activity or a therapeutically effective amount of the pharmaceutical composition described above.

In some embodiments, the method of preventing or treating a SARS-CoV-2 infection, comprising administering to a subject in need thereof a therapeutically effective amount of a first antibody or antigen-binding fragment thereof and a second antibody or antigen-binding fragment thereof of the antibody or antigen-binding fragment, as described above, wherein the first antibody or antigen-binding fragment thereof and the second antibody or antigen binding fragment thereof exhibit synergistic activity or a therapeutically effective amount of the pharmaceutical composition described above. In some embodiments, the first antibody or antigen-binding fragment thereof is administered before, after, or concurrently with the second antibody or antigen-binding fragment thereof.

In some embodiments, the first antibody or antigen-binding fragment thereof and the second antibody or antigen-binding fragment thereof can be any combinations of the antibody or antigen-binding fragment thereof comprising a heavy chain and a light chain that comprise the respective amino acid sequences described herein.

In some embodiments, the second therapeutic agent comprises an anti-inflammatory drug or an antiviral compound. In some embodiments, the antiviral compound comprises: a nucleoside analog, a peptoid, an oligopeptide, a polypeptide, a protease inhibitor, a 3C-like protease inhibitor, a papain-like protease inhibitor, or an inhibitor of an RNA dependent RNA polymerase. In some embodiments, the antiviral compound may include: acyclovir, gancyclovir, vidarabine, foscarnet, cidofovir, amantadine, ribavirin, trifluorothymidine, zidovudine, didanosine, zalcitabine, or an interferon. In some embodiments, the interferon is an interferon-α or an interferon-β.

In some embodiments, the antibody or antigen-binding fragment thereof is administered before, after, or concurrently with the second therapeutic agent or therapy. In some embodiments, the antibody or antigen-binding fragment thereof is administered to the subject intravenously, subcutaneously, or intraperitoneally. In some embodiments, the antibody or antigen-binding fragment thereof is administered prophylactically or therapeutically.

The antibodies described herein can be used together with one or more of other anti-SARS-CoV-2 virus antibodies to neutralize SARS-CoV-2 virus and thereby treating SARS-CoV-2 infections.

Combination Therapies

Combination therapies may include an anti-SARS-CoV-2 antibody of the invention and any additional therapeutic agent that may be advantageously combined with an antibody of the invention or with a biologically active fragment of an antibody of the invention. The antibodies of the present invention may be combined synergistically with one or more drugs or therapy used to treat a disease or disorder associated with a viral infection, such as a SARS-CoV-2 infection. In some embodiments, the antibodies of the invention may be combined with a second therapeutic agent to ameliorate one or more symptoms of said disease. In some embodiments, the antibodies of the invention may be combined with a second antibody to provide synergistic activity in ameliorating one or more symptoms of said disease. In some embodiments, the first antibody or antigen-binding fragment thereof is administered before, after, or concurrently with the second antibody or antigen-binding fragment thereof.

For example, the antibody described herein can be used in various detection methods for use in, e.g., monitoring the progression of a SARS-CoV-2 infection; monitoring patient response to treatment for such an infection, etc. The present disclosure provides methods of detecting a neuraminidase polypeptide in a biological sample obtained from an individual. The methods generally involve: a) contacting the biological sample with a subject anti-neuraminidase antibody; and b) detecting binding, if any, of the antibody to an epitope present in the sample. In some instances, the antibody comprises a detectable label. The level of neuraminidase polypeptide detected in the biological sample can provide an indication of the stage, degree, or severity of a SARS-CoV-2 infection. The level of the neuraminidase polypeptide detected in the biological sample can provide an indication of the individual's response to treatment for a SARS-CoV-2 infection.

In some embodiments, the second therapeutic agent is another antibody to a SARS-COV-2 protein or a fragment thereof. It is contemplated herein to use a combination ("cocktail") of antibodies with broad neutralization or inhibitory activity against SARS-COV-2. In some embodiments, non-competing antibodies may be combined and administered to a subject in need thereof. In some embodiments, the antibodies comprising the combination bind to distinct non-overlapping epitopes on the protein. In some embodiments, the second antibody may possess longer half-life in human serum.

As used herein, the term "in combination with" means that additional therapeutically active component(s) may be administered prior to, concurrent with, or after the administration of the anti-SARS-COV-2 antibody of the present invention. The term "in combination with" also includes sequential or concomitant administration of an anti-SARS-COV-2 antibody and a second therapeutic agent.

The additional therapeutically active component(s) may be administered to a subject prior to administration of an anti-SARS-COV-2 antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-SARS-COV-2 antibody of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-SARS-COV-2 antibody of the present invention. "Concurrent" administration, for purposes of the present invention, includes, e.g., administration of an anti-SARS-COV-2 antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-SARS-COV-2 antibody and the additional therapeutically active component may be administered intravenously, etc.); alternatively, each dosage form may be administered via a different route (e.g., the anti-SARS-COV-2 antibody may be administered intravenously, and the additional therapeutically active component may be administered orally). In any event, administering the components in a single dosage from, in separate dosage forms by the same route, or in separate dosage forms by different routes are all considered "concurrent administration," for purposes of the present disclosure. For purposes of the present disclosure, administration of an anti-SARS-COV-2 antibody "prior to," "concurrent with," or "after" (as those terms are defined hereinabove) administration of an additional therapeutically active component is considered administration of an anti-SARS-COV-2 antibody "in combination with" an additional therapeutically active component.

The present invention includes pharmaceutical compositions in which an anti-SARS-COV-2 antibody of the present invention is co-formulated with one or more of the additional therapeutically active component(s) as described elsewhere herein.

Administration Regimens

According to certain embodiments, a single dose of an anti-SARS-COV-2 antibody of the invention (or a pharmaceutical composition comprising a combination of an anti-SARS-COV-2 antibody and any of the additional therapeutically active agents mentioned herein) may be administered to a subject in need thereof. According to certain embodiments of the present invention, multiple doses of an anti-SARS-COV-2 antibody (or a pharmaceutical composition comprising a combination of an anti-SARS-COV-2 antibody and any of the additional therapeutically active agents mentioned herein) may be administered to a subject over a defined time course. The methods according to this aspect of the invention comprise sequentially administering to a subject multiple doses of an anti-SARS-COV-2 antibody of the invention. As used herein, "sequentially administering" means that each dose of anti-SARS-COV-2 antibody is administered to the subject at a different point in time, e.g., on different days separated by a predetermined interval (e.g., hours, days, weeks or months). The present invention includes methods which comprise sequentially administering to the patient a single initial dose of an anti-SARS-COV-2 antibody, followed by one or more secondary doses of the anti-SARS-COV-2 antibody, and optionally followed by one or more tertiary doses of the anti-SARS-COV-2 antibody.

The terms "initial dose," "secondary doses," and "tertiary doses," refer to the temporal sequence of administration of the anti-SARS-COV-2 antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-SARS-COV-2 antibody, but generally may differ from one another in terms of frequency of administration. In some embodiments, however, the amount of anti-SARS-COV-2 antibody contained in the initial, secondary and/or tertiary doses varies from one another (e.g., adjusted up or down as appropriate) during the course of treatment. In some embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 48 hours (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) after the immediately preceding dose. The phrase "the immediately preceding dose," as used herein, means, in a sequence of multiple administrations, the dose of anti-SARS-COV-2 antibody, which is administered to a patient prior to the administration of the very next dose in the sequence with no intervening doses.

The methods, according to this aspect of the invention, may comprise administering to a patient any number of secondary and/or tertiary doses of an anti-SARS-COV-2 antibody. For example, In some embodiments, only a single secondary dose is administered to the patient. In other embodiments, two or more (e.g., 2, 3, 4, 5, 6, 7, 8, or more) secondary doses are administered to the patient. Likewise, In some embodiments, only a single tertiary dose is administered to the patient. In other embodiments, two or more (e.g., 2, 3, 4, 5, 6, 7, 8, or more) tertiary doses are administered to the patient.

In some embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-SARS-COV-2 antibodies of the present invention may be used to detect and/or measure SARS-COV-2 in a sample, e.g., for diagnostic purposes. Some embodiments contemplate the use of one or more antibodies of the present invention in assays to detect a SARS-COV-2-associated-disease or disorder. Exemplary diagnostic assays for SARS-COV-2 may comprise, e.g., contacting a sample, obtained from a patient, with an anti-SARS-COV-2 antibody of the invention, wherein the anti-SARS-COV-2 antibody is labeled with a detectable label or reporter molecule or used as a capture ligand to selectively isolate SARS-COV-2 from patient samples. Alternatively, an unlabeled anti-SARS-COV-2 antibody can be used in diagnostic applications in combination with a secondary antibody, which is itself detectably labeled. The detectable label or reporter molecule can be a radioisotope, such as H, C, P, S, or I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure SARS-COV-2 in a sample include enzyme-linked immunosorbent assay (ELISA), radioimmunoassay (RIA), and fluorescence-activated cell sorting (FACS).

In another aspect, this disclosure further provides a method for detecting the presence of SARS CoV-2 in a sample comprising the steps of: (i) contacting a sample with the antibody or antigen-binding fragment thereof described above; and (ii) determining binding of the antibody or antigen-binding fragment to one or more SARS CoV-2 antigens, wherein binding of the antibody to the one or more SARS CoV-2 antigens is indicative of the presence of SARS CoV-2 in the sample.

In some embodiments, the SARS-CoV-2 antigen comprises a S polypeptide, such as a S polypeptide of a human or an animal SARS-CoV-2. In some embodiments, the SARS-CoV-2 antigen comprises the receptor-binding domain (RBD) of the S polypeptide. In some embodiments, the RBD comprises amino acids 319-541 of the S polypeptide.

In some embodiments, the antibody or antigen-binding fragment thereof is conjugated to a label. In some embodiments, the step of detecting comprises contacting a secondary antibody with the antibody or antigen-binding fragment thereof and wherein the secondary antibody comprises a label. In some embodiments, the label includes a fluorescent label, a chemiluminescent label, a radiolabel, and an enzyme.

In some embodiments, the step of detecting comprises detecting fluorescence or chemiluminescence. In some embodiments, the step of detecting comprises a competitive binding assay or ELISA.

In some embodiments, the method further comprises binding the sample to a solid support. In some embodiments, the solid support includes microparticles, microbeads, magnetic beads, and an affinity purification column.

Samples that can be used in SARS-COV-2 diagnostic assays according to the present invention include any tissue or fluid sample obtainable from a patient, which contains detectable quantities of either SARS-COV-2 protein, or fragments thereof, under normal or pathological conditions. Generally, levels of SARS-COV-2 protein in a particular sample obtained from a healthy patient (e.g., a patient not afflicted with a disease associated with SARS-COV-2) will be measured to initially establish a baseline, or standard, level of SARS-COV-2. This baseline level of SARS-COV-2 can then be compared against the levels of SARS-COV-2 measured in samples obtained from individuals suspected of having a SARS-COV-2-associated condition, or symptoms associated with such condition.

The antibodies specific for SARS-COV-2 protein may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

Definitions

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

The term "antibody" as referred to herein includes whole antibodies and any antigen-binding fragment or single chains thereof. Whole antibodies are glycoproteins comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, $C_L$. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The heavy chain variable region CDRs and FRs are HFR1, HCDR1, HFR2, HCDR2, HFR3, HCDR3, HFR4. The light chain variable region CDRs and FRs are LFR1, LCDR1, LFR2, LCDR2, LFR3, LCDR3, LFR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (CIq) of the classical complement system.

The term "antigen-binding fragment or portion" of an antibody (or simply "antibody fragment or portion"), as used herein, refers to one or more fragments of an antibody that retain the ability to specifically bind to an antigen (e.g., a Spike or S protein of SARS-CoV-2 virus). It has been shown that the antigen-binding function of an antibody can be performed by fragments of a full-length antibody. Examples of binding fragments encompassed within the term "antigen-binding fragment or portion" of an antibody include (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Fab' fragment, which is essentially a Fab with part of the hinge region (see, FUNDAMENTAL IMMUNOLOGY (Paul ed., 3rd ed. 1993)); (iv) a Fd fragment consisting of the VH and CHI domains; (v) a Fv fragment consisting of the VL and VH domains of a single arm of an antibody, (vi) a dAb fragment (Ward et al., (1989) Nature 341:544-546), which consists of a VH domain; (vii) an isolated CDR; and (viii) a nanobody, a heavy chain variable region containing a single variable domain and two constant domains. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv or scFv); see, e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment or portion" of an antibody. These antibody fragments are obtained using conventional techniques known to those with skill in the art, and the fragments are screened for utility in the same manner as are intact antibodies.

An "isolated antibody," as used herein, is intended to refer to an antibody that is substantially free of other antibodies having different antigenic specificities (e.g., an isolated antibody that specifically binds to a Spike or S protein of SARS-CoV-2 virus is substantially free of antibodies that specifically bind antigens other than the neuraminidase). An isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody" is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

The term "human monoclonal antibody" refers to antibodies displaying a single binding specificity, which have variable regions in which both the framework and CDR regions are derived from human germline immunoglobulin sequences. In one embodiment, the human monoclonal antibodies can be produced by a hybridoma that includes a B cell obtained from a transgenic nonhuman animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In some embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "isotype" refers to the antibody class (e.g., IgM or IgG1) that is encoded by the heavy chain constant region genes. The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody. The term "humanized antibody" is intended to refer to antibodies in which CDR sequences derived from the germline of another mammalian species, such as a mouse, have been grafted onto human framework sequences. Additional framework region modifications can be made within the human framework sequences.

The term "chimeric antibody" is intended to refer to antibodies in which the variable region sequences are derived from one species, and the constant region sequences are derived from another species, such as an antibody in which the variable region sequences are derived from a mouse antibody, and the constant region sequences are derived from a human antibody. The term can also refer to an antibody in which its variable region sequence or CDR(s) is derived from one source (e.g., an IgA1 antibody) and the constant region sequence or Fc is derived from a different source (e.g., a different antibody, such as an IgG, IgA2, IgD, IgE or IgM antibody).

The invention encompasses isolated or substantially purified nucleic acids, peptides, polypeptides or proteins. In the context of the present invention, an "isolated" nucleic acid, DNA or RNA molecule or an "isolated" polypeptide is a nucleic acid, DNA molecule, RNA molecule, or polypeptide that exists apart from its native environment and is therefore not a product of nature. An isolated nucleic acid, DNA molecule, RNA molecule or polypeptide may exist in a purified form or may exist in a non-native environment such as, for example, a transgenic host cell. A "purified" nucleic acid molecule, peptide, polypeptide or protein, or a fragment thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein, peptide or polypeptide that is substantially free of cellular material includes preparations of protein, peptide or polypeptide having less than about 30%, 20%, 10%, or 5% (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals.

The terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, pegylation, or any other manipulation, such as conjugation with a labeling component. As used herein, the term "amino acid" includes natural and/or unnatural or synthetic amino acids, including glycine and both the D or L optical isomers, and amino acid analogs and peptidomimetics.

A peptide or polypeptide "fragment" as used herein refers to a less than full-length peptide, polypeptide or protein. For example, a peptide or polypeptide fragment can have is at least about 3, at least about 4, at least about 5, at least about 10, at least about 20, at least about 30, at least about 40 amino acids in length, or single unit lengths thereof. For example, fragment may be 6, 7, 8, 9, 10, 11, 12, 13, 14, 15, 16, 17, or more amino acids in length. There is no upper limit to the size of a peptide fragment. However, in some embodiments, peptide fragments can be less than about 500 amino acids, less than about 400 amino acids, less than about 300 amino acids or less than about 250 amino acids in length. Preferably the peptide fragment can elicit an immune response when used to inoculate an animal. A peptide fragment may be used to elicit an immune response by inoculating an animal with a peptide fragment in combination with an adjuvant, a peptide fragment that is coupled to an adjuvant, or a peptide fragment that is coupled to arsanilic acid, sulfanilic acid, an acetyl group, or a picryl group. A peptide fragment can include a non-amide bond and can be a peptidomimetic.

As used herein, the term "conjugate" or "conjugation" or "linked" as used herein refers to the attachment of two or more entities to form one entity. A conjugate encompasses both peptide-small molecule conjugates as well as peptide-protein/peptide conjugates.

The term "recombinant," as used herein, refers to antibodies or antigen-binding fragments thereof of the invention created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

A "nucleic acid" or "polynucleotide" refers to a DNA molecule (for example, but not limited to, a cDNA or genomic DNA) or an RNA molecule (for example, but not limited to, an mRNA), and includes DNA or RNA analogs. A DNA or RNA analog can be synthesized from nucleotide analogs. The DNA or RNA molecules may include portions that are not naturally occurring, such as modified bases, modified backbone, deoxyribonucleotides in an RNA, etc. The nucleic acid molecule can be single-stranded or double-stranded.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions, and other modifications, including conservative amino acid substitutions. For instance, GCG software contains programs such as GAP and BESTFIT, which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

As used herein, the term "affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can generally be represented by the dissociation constant (KD). Affinity can be measured by common methods known in the art, including those described herein.

The term "specifically binds," or "binds specifically to," or the like, refers to an antibody that binds to a single epitope, e.g., under physiologic conditions., but which does not bind to more than one epitope. Accordingly, an antibody that specifically binds to a polypeptide will bind to an epitope that present on the polypeptide, but which is not present on other polypeptides. Specific binding can be characterized by an equilibrium dissociation constant of at least about $1\times10^{-8}$ M or less (e.g., a smaller KD denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to a Spike or S protein of SARS-CoV-2 virus.

Preferably, the antibody binds to a Spike or S protein with "high affinity," namely with a KD of 1×10-7 M or less, more preferably 5×10-8 M or less, more preferably 3×10-8 M or less, more preferably 1×10-8 M or less, more preferably 5×10-9 M or less or even more preferably 1×10-9 M or less, as determined by surface plasmon resonance, e.g., BIACORE. The term "does not substantially bind" to a protein or cells, as used herein, means does not bind or does not bind with a high affinity to the protein or cells, i.e., binds to the protein or cells with a KD of 1×10-6 M or more, more preferably 1×10-5 M or more, more preferably 1×10-4 M or more, more preferably 1×10-3 M or more, even more preferably 1×10-2 M or more.

The term "Kassoc" or "Ka," as used herein, is intended to refer to the association rate of a particular antibody-antigen interaction, whereas the term "Kdis" or "Kd," as used herein, is intended to refer to the dissociation rate of a particular antibody-antigenn interaction. The term "KD," as used herein, is intended to refer to the dissociation constant, which is obtained from the ratio of Kd to Ka (i.e., Kd/Ka) and is expressed as a molar concentration (M). KD values for antibodies can be determined using methods well established in the art. A preferred method for determining the KD of an antibody is by using surface plasmon resonance, preferably using a biosensor system such as a BIACORE system.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In some embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competition assays can be conducted as described, for example, in Ed Harlow and David Lane, Cold Spring Harb Protoc; 2006 or in Chapter 11 of "Using Antibodies" by Ed Harlow and David Lane, Cold Spring Harbor Laboratory Press, Cold Spring Harbor, NY, USA 1999. Competing antibodies bind to the same epitope, an overlapping epitope or to adjacent epitopes (e.g., as evidenced by steric hindrance). Other competitive binding assays include: solid phase direct or indirect radioimmunoassay (RIA), solid phase direct or indirect enzyme immunoassay (EIA), sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)).

The term "epitope" as used herein refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In some embodiments, epitopes may include determinants that are chemically active surface groupings of molecules such as amino acids, sugar side chains, phosphoryl groups, or sulfonyl groups, and, In some embodiments, may have specific three-dimensional structural characteristics, and/or specific charge characteristics. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immune-precipitation assays, wherein overlapping or contiguous peptides from a Spike or S protein are tested for reactivity with a given antibody. Methods of determining spatial conformation of epitopes include techniques in the art and those described herein, for example, x-ray crystallography and 2-dimensional nuclear magnetic resonance (see, e.g., Epitope Mapping Protocols in Methods in Molecular Biology, Vol. 66, G. E. Morris, Ed. (1996)).

The term "epitope mapping" refers to the process of identification of the molecular determinants for antibody-antigen recognition.

The term "binds to an epitope" or "recognizes an epitope" with reference to an antibody or antibody fragment refers to continuous or discontinuous segments of amino acids within an antigen. Those of skill in the art understand that the terms do not necessarily mean that the antibody or antibody fragment is in direct contact with every amino acid within an epitope sequence.

The term "binds to the same epitope" with reference to two or more antibodies means that the antibodies bind to the same, overlapping or encompassing continuous or discontinuous segments of amino acids. Those of skill in the art understand that the phrase "binds to the same epitope" does not necessarily mean that the antibodies bind to or contact exactly the same amino acids. The precise amino acids that the antibodies contact can differ. For example, a first antibody can bind to a segment of amino acids that is completely encompassed by the segment of amino acids bound by a second antibody. In another example, a first antibody binds one or more segments of amino acids that significantly overlap the one or more segments bound by the second antibody. For the purposes herein, such antibodies are considered to "bind to the same epitope."

As used herein, the term "immune response" refers to a biological response within a vertebrate against foreign agents, which response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell or a Th cell, such as a CD4+ or CD8+ T cell, or the inhibition of a Treg cell.

The term "detectable label" as used herein refers to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, streptavidin or haptens), intercalating dyes and the like. The term "fluorescer" refers to a substance or a portion thereof that is capable of exhibiting fluorescence in the detectable range.

In many embodiments, the terms "subject" and "patient" are used interchangeably irrespective of whether the subject has or is currently undergoing any form of treatment. As used herein, the terms "subject" and "subjects" may refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus monkey, chimpanzee, etc.) and a human). The subject may be a human or a non-human. In more exemplary aspects, the mammal is a human. As used herein, the expression "a subject in need thereof" or "a patient in need thereof" means a human or non-human mammal that exhibits one or more symptoms or indications of disorders (e.g., neuronal disorders, autoimmune diseases, and cardiovascular diseases), and/or who has been diagnosed with inflammatory disorders. In some embodiments, the subject is a mammal. In some embodiments, the subject is human.

As used herein, the term "disease" is intended to be generally synonymous and is used interchangeably with, the terms "disorder" and "condition" (as in medical condition), in that all reflect an abnormal condition (e.g., inflammatory disorder) of the human or animal body or of one of its parts that impairs normal functioning, is typically manifested by distinguishing signs and symptoms, and causes the human or animal to have a reduced duration or quality of life.

As used herein, the term "treating" or "treatment" of any disease or disorder refers in one embodiment, to ameliorating the disease or disorder (i.e., arresting or reducing the development of the disease or at least one of the clinical symptoms thereof). In another embodiment, "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

The terms "prevent," "preventing," "prevention," "prophylactic treatment" and the like refer to reducing the probability of developing a disorder or condition in a subject, who does not have, but is at risk of or susceptible to developing a disorder or condition.

The terms "decrease," "reduced," "reduction," "decrease," or "inhibit" are all used herein generally to mean a decrease by a statistically significant amount. However, for avoidance of doubt, "reduced," "reduction" or "decrease" or "inhibit" means a decrease by at least 10% as compared to a reference level, for example, a decrease by at least about 20%, or at least about 30%, or at least about 40%, or at least about 50%, or at least about 60%, or at least about 70%, or at least about 80%, or at least about 90% or up to and including a 100% decrease (e.g., absent level as compared to a reference sample), or any decrease between 10-100% as compared to a reference level.

As used herein, the term "agent" denotes a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent," which is a biologically, physiologically, or pharmacologically active substance (or substances) that acts locally or systemically in a subject.

As used herein, the terms "therapeutic agent," "therapeutic capable agent," or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder, or condition; and generally counteracting a disease, symptom, disorder or pathological condition.

The term "therapeutic effect" is art-recognized and refers to a local or systemic effect in animals, particularly mammals, and more particularly humans caused by a pharmacologically active substance.

The term "effective amount," "effective dose," or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A "prophylactically effective amount" or a "prophylactically effective dosage" of a drug is an amount of the drug that, when administered alone or in combination with another therapeutic agent to a subject at risk of developing a disease or of suffering a recurrence of disease, inhibits the development or recurrence of the disease. The ability of a therapeutic or prophylactic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

Doses are often expressed in relation to bodyweight. Thus, a dose which is expressed as [g, mg, or other unit]/kg (or g, mg etc.) usually refers to [g, mg, or other unit] "per kg (or g, mg etc.) bodyweight," even if the term "bodyweight" is not explicitly mentioned.

As used herein, the term "composition" or "pharmaceutical composition" refers to a mixture of at least one component useful within the invention with other components, such as carriers, stabilizers, diluents, dispersing agents, suspending agents, thickening agents, and/or excipients. The pharmaceutical composition facilitates administration of one or more components of the invention to an organism.

As used herein, the term "pharmaceutically acceptable" refers to a material, such as a carrier or diluent, which does not abrogate the biological activity or properties of the composition, and is relatively non-toxic, i.e., the material may be administered to an individual without causing undesirable biological effects or interacting in a deleterious manner with any of the components of the composition in which it is contained.

As used herein, the term "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation and not injurious to the subject. Some examples of materials that may serve as pharmaceutically acceptable carriers include: sugars, such as lactose, glucose, and sucrose; starches, such as corn starch and potato starch; cellulose, and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of one or more components of the invention, and are physiologically acceptable to the subject. Supplementary active compounds may also be incorporated into the compositions.

"Combination" therapy, as used herein, unless otherwise clear from the context, is meant to encompass administration of two or more therapeutic agents in a coordinated fashion and includes, but is not limited to, concurrent dosing. Specifically, combination therapy encompasses both co-administration (e.g., administration of a co-formulation or simultaneous administration of separate therapeutic compositions) and serial or sequential administration, provided that administration of one therapeutic agent is conditioned in some way on the administration of another therapeutic agent. For example, one therapeutic agent may be administered only after a different therapeutic agent has been administered and allowed to act for a prescribed period of time. See, e.g., Kohrt et al. (2011) Blood 117:2423.

As used herein, the term "co-administration" or "co-administered" refers to the administration of at least two agent(s) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

As used herein, the term "contacting," when used in reference to any set of components, includes any process whereby the components to be contacted are mixed into the same mixture (for example, are added into the same compartment or solution), and does not necessarily require actual physical contact between the recited components. The recited components can be contacted in any order or any combination (or sub-combination) and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C.

"Sample," "test sample," and "patient sample" may be used interchangeably herein. The sample can be a sample of serum, urine plasma, amniotic fluid, cerebrospinal fluid, cells, or tissue. Such a sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. The terms "sample" and "biological sample" as used herein generally refer to a biological material being tested for and/or suspected of containing an analyte of interest such as antibodies. The sample may be any tissue sample from the subject. The sample may comprise protein from the subject.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism, such as a non-human animal.

As used herein, the singular forms "a," "an," and "the" include plural references unless the context clearly dictates otherwise.

As used herein, the terms "including," "comprising," "containing," or "having" and variations thereof are meant to encompass the items listed thereafter and equivalents thereof as well as additional subject matter unless otherwise noted.

As used herein, the phrases "in one embodiment," "in various embodiments," "in some embodiments," and the like are used repeatedly. Such phrases do not necessarily refer to the same embodiment, but they may unless the context dictates otherwise.

As used herein, the terms "and/or" or "/" means any one of the items, any combination of the items, or all of the items with which this term is associated.

As used herein, the word "substantially" does not exclude "completely," e.g., a composition which is "substantially free" from Y may be completely free from Y. Where necessary, the word "substantially" may be omitted from the definition of the invention.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise. In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1

This example describes the materials and methods used in the subsequent EXAMPLES below.

Study Participants.

To isolate and characterize anti-SARS-CoV-2 RBD antibodies from vaccinees, a cohort of 20 individuals that participated in either the Moderna or Pfizer/BioNTech phase 3 vaccine clinical trial and no prior history of SARS-CoV-2 infection were recruited at the NIH Blood Center and the Rockefeller University Hospital for blood donation. Eligible participants included adults at least 18 years of age with no known heart, lung, kidney disease, or bleeding disorders, no history of HIV-1 or malaria infection. All participants were asymptomatic at the time of the study visit and had received a complete two-dose regimen of either mRNA vaccine. Informed consent was obtained from all participants, and the study was conducted in accordance with Good Clinical Practice. The study visits and blood draws were reviewed and approved under the National Institutes of Health's Federalwide Assurance (FWA00005897) in accordance with Federal regulations 45 CFR 46 and 21 CFR 5 by the NIH Intramural Research Program IRB committee (IRB #99CC0168, Collection and Distribution of Blood Components from Healthy Donors for In vitro Research Use) and by the Institutional Review Board of the Rockefeller University (IRB #DRO-1006, Peripheral Blood of Coronavirus Survivors to Identify Virus-Neutralizing Antibodies). For detailed participant characteristics, see Table 1.

Blood Samples Processing and Storage.

Samples collected at NIH were drawn from participants at the study visit and processed within 24 hours. Briefly, whole blood samples were subjected to Ficoll gradient centrifugation after 1:1 dilution in PBS. Plasma and PBMC samples were obtained through phase separation of plasma layer and Buffy coat phase, respectively. PBMCs were further prepared through centrifugation, red blood cells lysis, and washing steps, and stored in CellBanker cell freezing media (Amsbio). All samples were aliquoted and stored at −80° C. and shipped on dry ice. Prior to experiments, aliquots of plasma samples were heat-inactivated (56° ° C. for 1 hour) and then stored at 4° C. Peripheral Blood Mononuclear Cells (PBMCs) obtained from samples collected at Rockefeller University were purified as previously reported (Gaebler, C. et al. bioRxiv, (2020); Robbiani, D. F. et al. Nature 584, 437-442 (2020)) by gradient centrifugation and stored in liquid nitrogen in the presence of FCS and DMSO. Heparinized plasma samples were aliquoted and stored at −20 C or less. Prior to experiments, aliquots of plasma samples were heat-inactivated (56 C for 1 hour) and then stored at 4° C.

ELISAs

ELISAs to evaluate antibodies binding to SARS-CoV-2 S (BioHub), RBD, and additional mutated RBDs were performed by coating high-binding 96-half-well plates (Corning 3690) with 50 µl per well of a 1 µg/ml protein solution in PBS overnight at 4° C. Plates were washed 6 times with washing buffer (1×PBS with 0.05% Tween-20 (Sigma-Aldrich)) and incubated with 170 µl per well blocking buffer (1×PBS with 2% BSA and 0.05% Tween-20 (Sigma)) for 1 h at room temperature. Immediately after blocking, monoclonal antibodies or plasma samples were added in PBS and incubated for 1 h at room temperature. Plasma samples were assayed at a 1:66.6 (RU samples) or a 1:33.3 (NIH samples) starting dilution and 7 additional threefold serial dilutions. Monoclonal antibodies were tested at 10 µg/ml starting concentration and 10 additional fourfold serial dilutions. Plates were washed 6 times with washing buffer and then incubated with anti-human IgG, IgM, or IgA secondary antibody conjugated to horseradish peroxidase (HRP) (Jackson Immuno Research 109-036-088 109-035-129 and Sigma A0295) in blocking buffer at a 1:5,000 dilution (IgM and IgG) or 1:3,000 dilution (IgA). Plates were developed by addition of the HRP substrate, TMB (ThermoFisher) for 10 min (plasma samples) or 4 minutes (monoclonal antibodies), then the developing reaction was stopped by adding 50 µl 1 M $H_2SO_4$ and absorbance was measured at 450 nm with an ELISA microplate reader (FluoStar Omega, BMG Labtech) with Omega and Omega MARS software for analysis. For plasma samples, a positive control (plasma from participant COV72 (Gaebler, C. et al. bioRxiv, (2020); Robbiani, D. F. et al. Nature 584, 437-442 (2020)), diluted 66.6-fold and with seven additional threefold serial dilutions in PBS) was added to every assay plate for validation. The average of its signal was used for normalization of all of the other values on the same plate with Excel software before calculating the area under the curve using Prism V8.4 (GraphPad). For monoclonal antibodies, the EC50 was determined using four-parameter nonlinear regression (GraphPad Prism V8.4).

Expression of RBD Proteins

Mammalian expression vectors encoding the RBDs of SARS-CoV-2 (GenBank MN985325.1; S protein residues 319-539) and eight additional mutant RBD proteins (E484K, Q493R, R346S, N493K, N440K, V367F, A475V, S477N, and V483A) with an N-terminal human IL-2 or Mu phosphatase signal peptide were previously described (Barnes, C. O. et al. Cell 182, 828-842 e816 (2020)).

Cells and Viruses

293T/ACE2.cl22 and HT1080 ACE2.cl14 cells (Schmidt, F. et al. J Exp Med 217 (2020)) were cultured in Dulbecco's Modified Eagle Medium (DMEM) supplemented with 10% fetal bovine serum (FBS) at 37° C. and 5% $CO_2$. Cells were periodically tested for contamination with mycoplasma or retroviruses.

rVSV/SARS-CoV-2/GFP chimeric virus stocks were generated by infecting 293T/ACE2.cl22 cells. The supernatant was harvested 1 day post infection (dpi), cleared of cellular debris, and stored at −80° C. A plaque purified variant designated rVSV/SARS-CoV-2/GFP$_{2E1}$ that encodes D215G/R683G substitutions was used in these studies.

Selection and Analysis of Antibody Escape Mutations

For the selection of monoclonal antibody-resistant spike variants, an rVSV/SARS-CoV-2/GFP$_{2E1}$ (Schmidt, F. et al. J Exp Med 217 (2020)) population containing 106 infectious units was incubated with monoclonal antibodies (10 µg/ml passage 10-40 µg/ml for 1 hr at 37° C. Then, the virus-antibody mixtures were incubated with 5×10$^5$ 293T/ACE2cl.22 cells in 6-well plates. At 1 day post infection, media was replaced with fresh media containing the equivalent concentrations of antibodies. The supernatant was harvested 2 days after infection, and 150 µl of the cleared supernatant was used to infect cells for passage 2, while 150 µl was subjected to RNA extraction and sequencing.

For identification of putative antibody resistance mutations, RNA was extracted using NucleoSpin 96 Virus Core Kit (Macherey-Nagel). The RNA was reversed transcribed using the SuperScript VILO cDNA Synthesis Kit (Thermo Fisher Scientific). KOD Xtreme Hot Start DNA Polymerase (Millipore Sigma) was used for amplification of cDNA using primers flanking the S-encoding sequence. The PCR products were purified and sequenced as previously described (Weisblum, Y. et al. Elife 9 (2020)). Briefly, tagmentation reactions were performed using 1 ul diluted cDNA, 0.25 µl Nextera TDE1 Tagment DNA enzyme (catalog no. 15027865), and 1.25 µl TD Tagment DNA buffer (catalog no. 15027866; Illumina). Next, the DNA was ligated to unique i5/i7 barcoded primer combinations using the Illumina Nextera XT Index Kit v2 and KAPA HiFi HotStart ReadyMix (2×; KAPA Biosystems) and purified using AmPure Beads XP (Agencourt), after which the samples were pooled into one library and subjected to paired-end sequencing using Illumina MiSeq Nano 300 V2 cycle kits (Illumina) at a concentration of 12 pM.

For analysis of the sequencing data, the raw paired-end reads were pre-processed to remove trim adapter sequences and to remove low-quality reads (Phred quality score <20) using BBDuk. Reads were mapped to the rVSV/SARS-CoV-2/GFP sequence using Geneious Prime (Version 2020.1.2). Mutations were annotated using Geneious Prime, with a P-value cutoff of 10 6.

SARS-CoV-2 Pseudotyped Reporter Virus

A panel of plasmids expressing RBD-mutant SAR-COV-2 spike proteins in the context of pSARS-CoV-2-$S_{\Delta 19}$ have been described previously (Weisblum, Y. et al. Elife 9 (2020)). Additional substitutions were introduced using either PCR primer-mediated mutagenesis or with synthetic gene fragments (IDT) followed by Gibson assembly. The mutants E484K and KEN (K417N+E484K+N501Y) were constructed in the context of a pSARS-CoV-2-$S_{\Delta 19}$ variant with a mutation in the furin cleavage site (R683G). The NT50s and IC50 of these pseudotypes were compared to a wildtype SARS-CoV-2 (NC_045512) spike sequence carrying R683G in the subsequent analyses, as appropriate.

Generation of SARS-CoV-2 pseudotyped HIV-1 particles was performed as previously described (Robbiani, D. F. et al. Nature 584, 437-442 (2020)). Briefly, 293T cells were transfected with pNL4-3ΔEnv-nanoluc and pSARS-CoV-2-$S_{\Delta 19}$ and pseudotyped virus stocks were harvested 48 hours after transfection, filtered, and stored at −80° C.

SARS-CoV-2 Pseudotype Neutralization Assays

Plasma or monoclonal antibodies from vaccine recipients were four-fold or five-fold serially diluted and then incubated with SARS-CoV-2 pseudotyped HIV-1 reporter virus for 1 h at 37° C. The antibody and pseudotype virus mixture was added to $293T_{Ace2}$ cells (Robbiani, D. F. et al. Nature 584, 437-442 (2020)) (for comparisons of plasma from COVID-19-convalescents and vaccine recipients) or HT1080ACE2.cl14 cells (for analysis of spike mutants with vaccine recipient plasma or monoclonal antibodies). After 48 h, cells were washed with PBS and lysed with Luciferase Cell Culture Lysis 5× reagent (Promega), and Nanoluc Luciferase activity in lysates was measured using the Nano-Glo Luciferase Assay System (Promega) with the Glomax Navigator (Promega). The relative luminescence units were normalized to those derived from cells infected with SARS-CoV-2 pseudotyped virus in the absence of plasma or monoclonal antibodies. The half-maximal neutralization titers for plasma ($NT_{50}$) or half-maximal and 90% inhibitory concentrations for monoclonal antibodies ($IC_{50}$ and $IC_{90}$, respectively) were determined using four-parameter nonlinear regression (least-squares regression method without weighting; constraints: top=1, bottom=0) (GraphPad Prism).

Biotinylation of Viral Protein for Use in Flow Cytometry

Purified and Avi-tagged SARS-CoV-2 RBD was biotinylated using the Biotin-Protein Ligase-BIRA kit according to manufacturer's instructions (Avidity) as described before (Robbiani, D. F. et al. Nature 584, 437-442 (2020)). Ovalbumin (Sigma, A5503-1G) was biotinylated using the EZ-Link Sulfo-NHS-LC-Biotinylation kit according to the manufacturer's instructions (Thermo Scientific). Biotinylated ovalbumin was conjugated to streptavidin-BV711 (BD biosciences, 563262) and RBD to streptavidin-PE (BD Biosciences, 554061) and streptavidin-AF647 (Biolegend, 405237).

Flow Cytometry and Single Cell Sorting

Single-cell sorting by flow cytometry was performed as described previously (Robbiani, D. F. et al. Nature 584, 437-442 (2020)). Briefly, peripheral blood mononuclear cells were enriched for B cells by negative selection using a pan-B-cell isolation kit according to the manufacturer's instructions (Miltenyi Biotec, 130-101-638). The enriched B cells were incubated in FACS buffer (1×PBS, 2% FCS, 1 mM EDTA) with the following anti-human antibodies (all at 1:200 dilution): anti-CD20-PECy7 (BD Biosciences, 335793), anti-CD3-APC-eFluro 780 (Invitrogen, 47-0037-41), anti-CD8-APC-eFluor 780 (Invitrogen, 47-0086-42), anti-CD16-APC-eFluor 780 (Invitrogen, 47-0168-41), anti-CD14-APC-eFluor 780 (Invitrogen, 47-0149-42), as well as Zombie NIR (BioLegend, 423105) and fluorophore-labelled RBD and ovalbumin (Ova) for 30 min on ice. Single CD3−CD8−CD14−CD16−CD20+Ova−RBD-PE+RBD-AF647+ B cells were sorted into individual wells of 96-well plates containing 4 μl of lysis buffer (0.5×PBS, 10 mM DTT, 3,000 units/ml RNasin Ribonuclease Inhibitors (Promega, N2615) per well using a FACS Aria III and FACSDiva software (Becton Dickinson) for acquisition and FlowJo for analysis. The sorted cells were frozen on dry ice, and then stored at −80° C. or immediately used for subsequent RNA reverse transcription.

Antibody Sequencing, Cloning, and Expression

Antibodies were identified and sequenced as described previously (Robbiani, D. F. et al. Nature 584, 437-442 (2020)). In brief, RNA from single cells was reverse-transcribed (SuperScript III Reverse Transcriptase, Invitrogen, 18080-044), and the cDNA was stored at −20° C. or used for subsequent amplification of the variable IGH, IGL, and IGK genes by nested PCR and Sanger sequencing. Sequence analysis was performed using MacVector. Amplicons from the first PCR reaction were used as templates for sequence- and ligation-independent cloning into antibody expression vectors. Recombinant monoclonal antibodies and Fabs were produced and purified as previously described (Robbiani, D. F. et al. Nature 584, 437-442 (2020)).

Cryo-EM Sample Preparation

Expression and purification of SARS-CoV-2 6P stabilized S trimers was conducted as previously described ((Hsieh, C. L. et al. Science 369, 1501-1505 (2020); Cohen, A. A. et al. bioRxiv, doi: 10.1101/2020.11.17.387092 (2020)). Purified Fab and S 6P trimer were incubated at a 1.1:1 molar ratio per protomer on ice for 30 minutes prior to deposition on a freshly glow-discharged 300 mesh, 1.2/1.3 Quantifoil copper grid. Immediately before 3 μl of the complex was applied to the grid, fluorinated octyl-malotiside was added to the Fab-S complex to a final detergent concentration of 0.02% w/v, resulting in a final complex concentration of 3 mg/ml. Samples were vitrified in 100% liquid ethane using a Mark IV Vitrobot after blotting for 3 s with Whatman No. 1 filter paper at 22° C. and 100% humidity.

Cryo-EM Data Collection and Processing

Data collection and processing followed a similar workflow to what has been previously described in detail (Barnes, C. O. et al. Nature 588, 682-687 (2020)). Micrographs were collected on a Talos Arctica transmission electron microscope (Thermo Fisher) operating at 200 kV for all Fab-S complexes. Data were collected using SerialEM automated data collection software (Mastronarde, D. N. J Struct Biol 152, 36-51 (2005)) and movies were recorded with a K3 camera (Gatan). For all datasets, cryo-EM movies were patch motion corrected for beam-induced motion including dose-weighting within cryoSPARC v2.15 (Punjani, A., et al. Nat Methods 14, 290-296 (2017).) after binning super resolution movies. The non-dose-weighted images were used to estimate CTF parameters using cryoSPARC implementation of the Patch CTF job. Particles were picked using Blob picker and extracted 4× binned and 2D classified. Class averages corresponding to distinct views with secondary structure features were chosen, and ab initio models were generated. 3D classes that showed features of a Fab-S complex were re-extracted, unbinned (0.869 Å/pixel), and homogenously refined with C1 symmetry. Overall resolutions were reported based on gold standard FSC calculations.

Cryo-EM Structure Modeling and Refinement

Coordinates for initial complexes were generated by docking individual chains from reference structures into cryo-EM density using UCSF Chimera (Goddard, T. D. et al. Protein Sci 27, 14-25 (2018)) (S trimer: PDB 7KXL, Fab: PDB 6XCA or 7K8P after trimming CDR3 loops and converting to a polyalanine model). Models were then refined into cryo-EM maps by rigid body and real space refinement in Phenix (Terwilliger, T. C., et al. Nat Methods 15, 905-908 (2018)) If the resolution allowed, partial CDR3 loops were built manually in Coot (Emsley, P., et al. Acta Crystallogr D Biol Crystallogr 66, 486-501(2010)) and then refined using real-space refinement in Phenix.

Computational Analyses of Antibody Sequences

Antibody sequences were trimmed based on quality and annotated using Igblastn v.1.14. with IMGT domain delineation system. Annotation was performed systematically using Change-O toolkit v.0.4.540 (Gupta, N. T. et al. Bioinformatics 31, 3356-3358 (2015)). Heavy and light chains derived from the same cell were paired, and clonotypes were assigned based on their V and J genes using in-house R and Perl scripts (Extended data FIG. 2). All scripts and the data used to process antibody sequences publicly are available on GitHub (https://github.com/stratust/igpipeline).

The frequency distributions of human V genes in anti-SARS-CoV-2 antibodies from this study were compared to 131,284,220 IgH and IgL sequences generated by and downloaded from cAb-Rep (Guo, Y., et al. Front Immunol 10, 2365 (2019).), a database of human shared BCR clonotypes available at https://cab-rep.c2b2.columbia.edu/. Based on the 97 distinct V genes that make up the 4186 analyzed sequences from Ig repertoire of the 14 participants present in this study, the IgH and IgL sequences were selected from the database that are partially coded by the same V genes and counted them according to the constant region. The frequencies shown in (FIG. 2e and Extended Data FIG. 3a) are relative to the source, and isotype analyzed. The two-sided binomial test was used to check whether the number of sequences belonging to a specific IgHV or IgLV gene in the repertoire is different according to the frequency of the same IgV gene in the database. Adjusted p-values were calculated using the false discovery rate (FDR) correction. Significant differences are denoted with stars.

Nucleotide somatic hypermutation and CDR3 length were determined using in-house R and Perl scripts. For somatic hypermutations, IGHV and IGLV nucleotide sequences were aligned against their closest germlines using Igblastn, and the number of differences were considered nucleotide mutations. The average mutations for V genes were calculated by dividing the sum of all nucleotide mutations across all participants by the number of sequences used for the analysis. To calculate the GRAVY scores of hydrophobicity (Kyte, J. & Doolittle, R. F. J Mol Biol 157, 105-132 (1982)), Guy H. R. Hydrophobicity scale was used based on free energy of transfer (kcal/mole) implemented by the R package Peptides (the Comprehensive R Archive Network repository; https://journal.r-project.org/archive/2015/RJ-2015-001/RJ-2015-001.pdf). 1405 heavy chain CDR3 amino acid sequences from this study and 22,654,256 IGH CDR3 sequences from the public database of memory B cell receptor sequences were used. The two-tailed Wilcoxon nonparametric test was used to test whether there is a difference in hydrophobicity distribution.

Data Availability Statement:

The raw sequencing data and computer scripts associated with FIG. 2 have been deposited at Github (https://github.com/stratust/igpipeline). This study also uses data from "A Public Database of Memory and Naive B-Cell Receptor Sequences" (DeWitt, W. S. et al. PLOS One 11, e0160853 (2016)), PDB (6VYB and 6NB6) and from "High frequency of shared clonotypes in human B cell receptor repertoires" (Soto, C. et al. Nature 566, 398-402 (2019)). Cryo-EM maps associated with data reported in this manuscript are deposited in the Electron Microscopy Data Bank (EMDB: https://www.ebi.ac.uk/pdbe/emdb/).

Example 2

To date, severe acute respiratory syndrome coronavirus-2 (SARS-CoV-2) has infected nearly 100 million individuals resulting in almost two million deaths. Many vaccines are being deployed to prevent the disease, including two novel mRNA-based vaccines (Gaebler, C. & Nussenzweig, M. C. Nature 586, 501-502 (2020); Krammer, F. Nature 586, 516-527 (2020)). These vaccines elicit neutralizing antibodies and appear to be safe and effective, but the precise nature of the elicited antibodies is not known. Here, the antibody and memory B cell responses in a cohort of 20 volunteers who received either the Moderna (mRNA-1273) or Pfizer-BioNTech (BNT162b2) vaccines were reported. Consistent with prior reports, 8 weeks after the second vaccine injection, the volunteers showed high levels of IgM, and IgG anti-SARS-CoV-2 spike protein (S), receptor binding domain (RBD) binding titers. Moreover, the plasma neutralizing activity and the relative numbers of RBD-specific memory B cells were equivalent to individuals who recovered from natural infection. However, activity against SARS-CoV-2 variants encoding E484K or N501Y or the K417N:E484K:N501Y combination was reduced by a small but significant margin. Consistent with this finding, vaccine-elicited monoclonal antibodies (mAbs) potently neutralize SARS-CoV-2, targeting a number of different RBD epitopes. However, neutralization by 9 of the 17 most potent mAbs tested was reduced or abolished by either K417N, E484K, or N501Y mutations. Notably, the same mutations were selected when recombinant vesicular stomatitis virus (rVSV)/SARS-CoV-2 S was cultured in the presence of the vaccine-elicited mAbs. Thus vaccine- and virus-encoded S adopts similar conformations to induce equivalent anti-RBD antibodies. Taken together, the results indicate that the antibodies in clinical 20) use should be tested against newly arising variants, and that mRNA vaccines may need to be updated periodically.

Between Oct. 19, 2020 and Jan. 15, 2021, 20 volunteers who received two doses of the Moderna (n=14) or Pfizer mRNA (n=6) vaccines were recruited for blood donation and analyzed. Ages of the analyzed volunteers ranged from 29-69 years (median 43); 12 (60%) were male and 8 (40%) female. 16 participants identified as Caucasian, 2 as Hispanic, and 1 as African American or Asian, respectively. The time from the second vaccination to sample collection varied between 3-14 weeks with an average of 8 weeks. None of the volunteers had a history of prior SARS-CoV-2 infection, and none reported serious adverse events after vaccination (Table 1).

Vaccine Plasma Binding and Neutralizing Activity Against SARS-CoV-2

Plasma IgM and IgG anti-SARS-CoV-2 S and RBD were measured by enzyme-linked immunosorbent assay (ELISA). All individuals tested showed reactivity to S and RBD that was significantly higher compared to pre-COVID-19 historic controls (FIG. 5). Anti-S and -RBD IgG levels were higher than IgM or IgA. Moreover, there was greater variability in the anti-RBD than the anti-S response, but the two were positively correlated (FIG. 5).

Plasma neutralizing activity was determined using HIV-1 pseudotyped with SARS-CoV-2 S protein. There was a broad range of plasma neutralizing activity 3-14 weeks after the second vaccine dose that was similar to that elicited by natural infection in a mild disease cohort after 1.3 months and greater than the activity at 6.2 months after infection (FIG. 1a; Table 1). There was no significant difference in neutralizing activity between Moderna and Pfizer vaccines (FIG. 1b). Plasma neutralizing activity was directly correlated to anti-S and -RBD binding titers in ELISAs (FIGS. 1c-d and FIGS. 6a-d). Finally, RBD and S binding and neutralizing activities were directly correlated to the time between receiving the first dose and blood donation with significantly lower levels in all three measurements with time (FIGS. 1e-g, and FIGS. 6e-h).

To determine whether plasma from vaccinated individuals can neutralize circulating SARS-CoV-2 variants of concern and mutants that arise in vitro under antibody pressure, w vaccinee plasma was tested against a panel of 10 mutant pseudotype viruses, including recently-reported N501Y (B1.1.7 variant), K417N, E484K and the combination of these 3 RBD mutations (501Y.V2 variant). Vaccinee plasma was significantly less effective in neutralizing the HIV-1 virus pseudotyped with certain SARS-CoV-2 mutant S proteins (FIGS. 1e and f and Extended Data FIG. 2). Among the volunteer plasmas tested, there was a 1 to 3, 1.3 to 2.5, and 1.1 to 3 fold decrease in neutralizing activity against E484K, N501Y, and the K417N:E484K:N501Y combination, respectively (p=0.008, p=0.003, and p=0.002 respectively, FIGS. 1h and i). It was concluded that the plasma neutralizing activity elicited by mRNA vaccination is variably but significantly less effective against particular RBD mutants in the tested panel.

Vaccine-Elicited SARS-CoV-2 RBD-Specific Monoclonal Antibodies

Although circulating antibodies derived from plasma cells wane over time, long-lived immune memory can persist in expanded clones of memory B cells. Flow cytometry was used to enumerate the circulating SARS-CoV-2 RBD-specific memory B cells elicited by mRNA immunization (FIG. 2a and FIGS. 7a-b). Notably, the percentage of RBD-binding memory B cells in vaccinees was significantly greater than in naturally infected individuals assayed after 1.3 months, but similar to the same individuals assayed after 6.2 months (FIG. 2b). The percentage of RBD-binding memory B cells in vaccinees was not correlated to the time after vaccination FIG. 7c). Thus, mRNA vaccination elicits a robust SARS-CoV-2 RBD-specific B cell memory response that resembles natural infection.

Figure 8A:
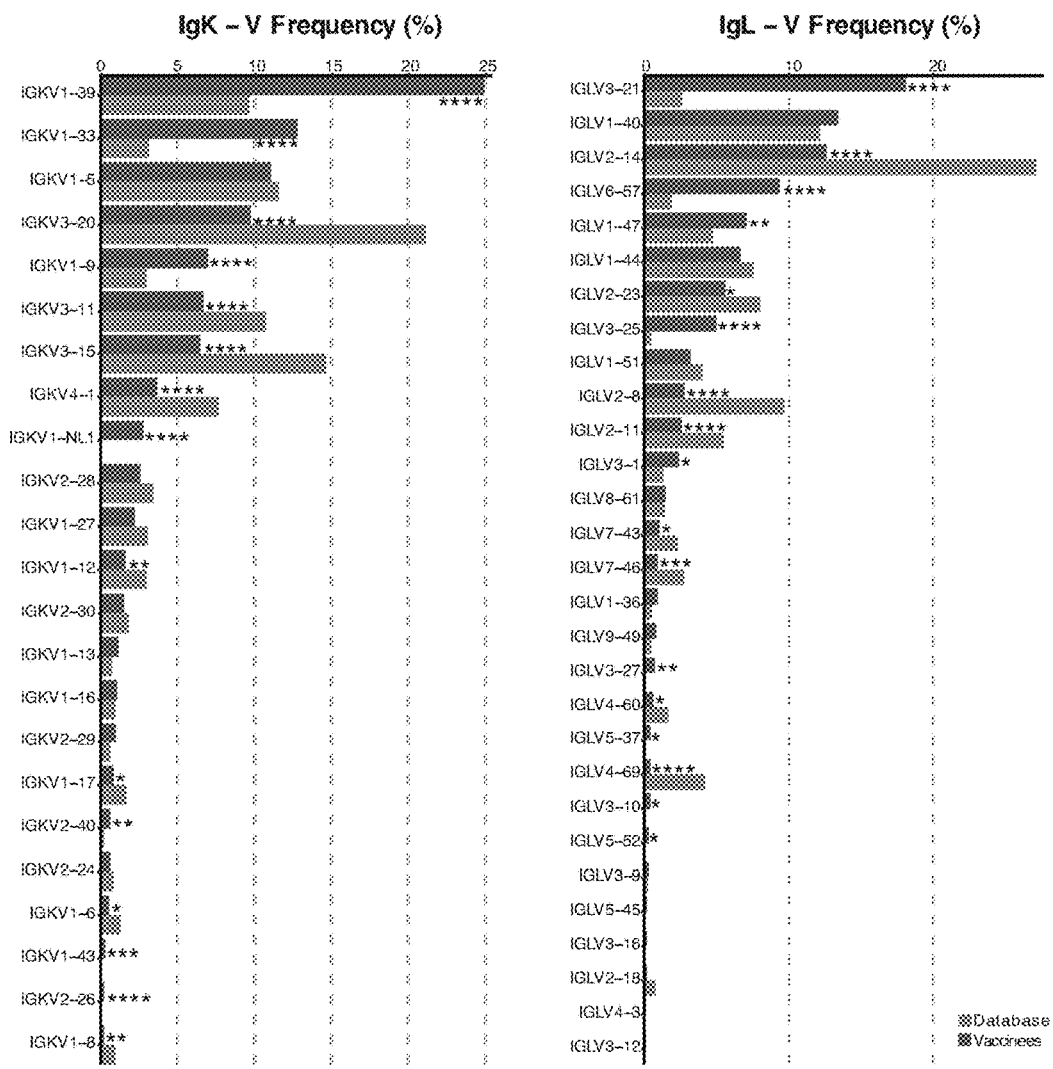
FIGS. 8a and 8b are a set of diagrams showing frequency distributions of human $V_L$ genes.
Figure 8B:
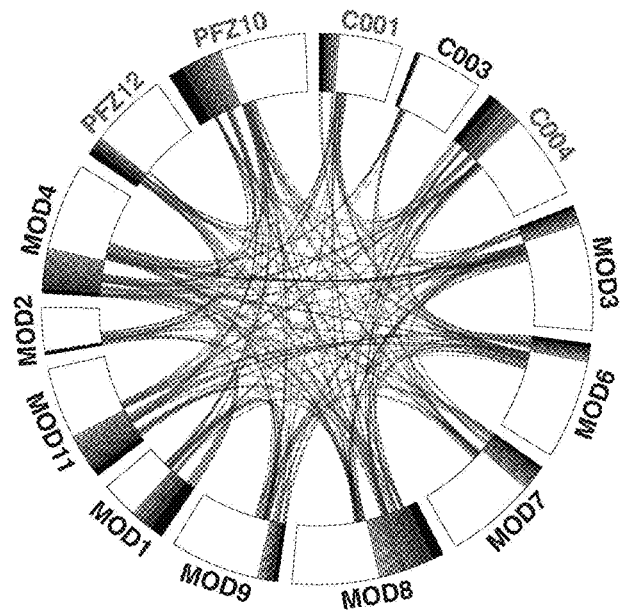
Figures 9A, 9B:
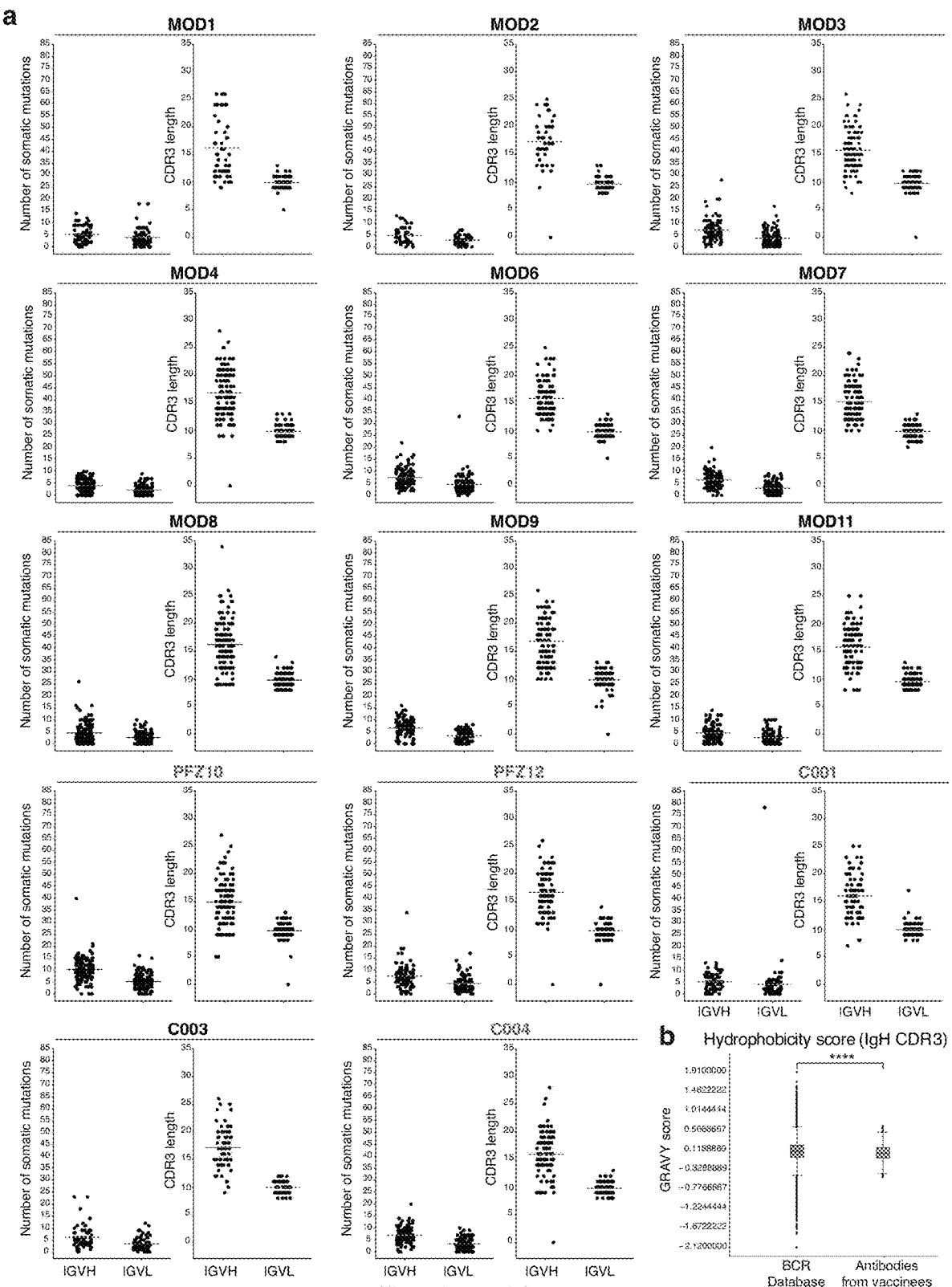
FIGS. 9a and 9b are a set of diagrams showing antibody somatic hypermutation and CDR3 length.

To examine the nature of the antibodies produced by memory B cells in response to vaccination, 1,409 paired antibody heavy and light chains were obtained from RBD binding single B cells from 14 individuals (n=10 Moderna and n=4 Pfizer vaccinees) (Table 2). Expanded clones of cells comprised 4-50% of the overall RBD binding memory B cell compartment (FIGS. 2-d and FIG. 7d). Similar to natural infection, IGVH 3-53, and 3-30 and some IGVL genes were significantly over-represented in the RBD-binding memory B cell compartment of vaccinated individuals (FIG. 2e and FIG. 8a). In addition, antibodies that share the same combination of IGHV and IGLV genes in vaccinees comprised 39% of all the clonal sequences (FIG. 8b) and 59% when combined with naturally infected individuals (FIG. 2f), and some of these antibodies were nearly identical (Tables 2 and 3). The number of V gene nucleotide mutations in vaccinees is greater than in naturally infected individuals assayed after 1.3 months, but lower than that in the same individuals assayed after 6.2 months (FIG. 2g and FIG. 9a). The length of the IgH CDR3 was similar in both naturally infected individuals and vaccinees, and hydrophobicity was below average (FIG. 2h and FIGS. 9a-b). Thus, the IgG memory response is similar in individuals receiving the Pfizer and Moderna vaccines, and both are rich in recurrent and clonally expanded antibody sequences.

Figures 10D, 10E, 10F, 10G, 10K, 10L:
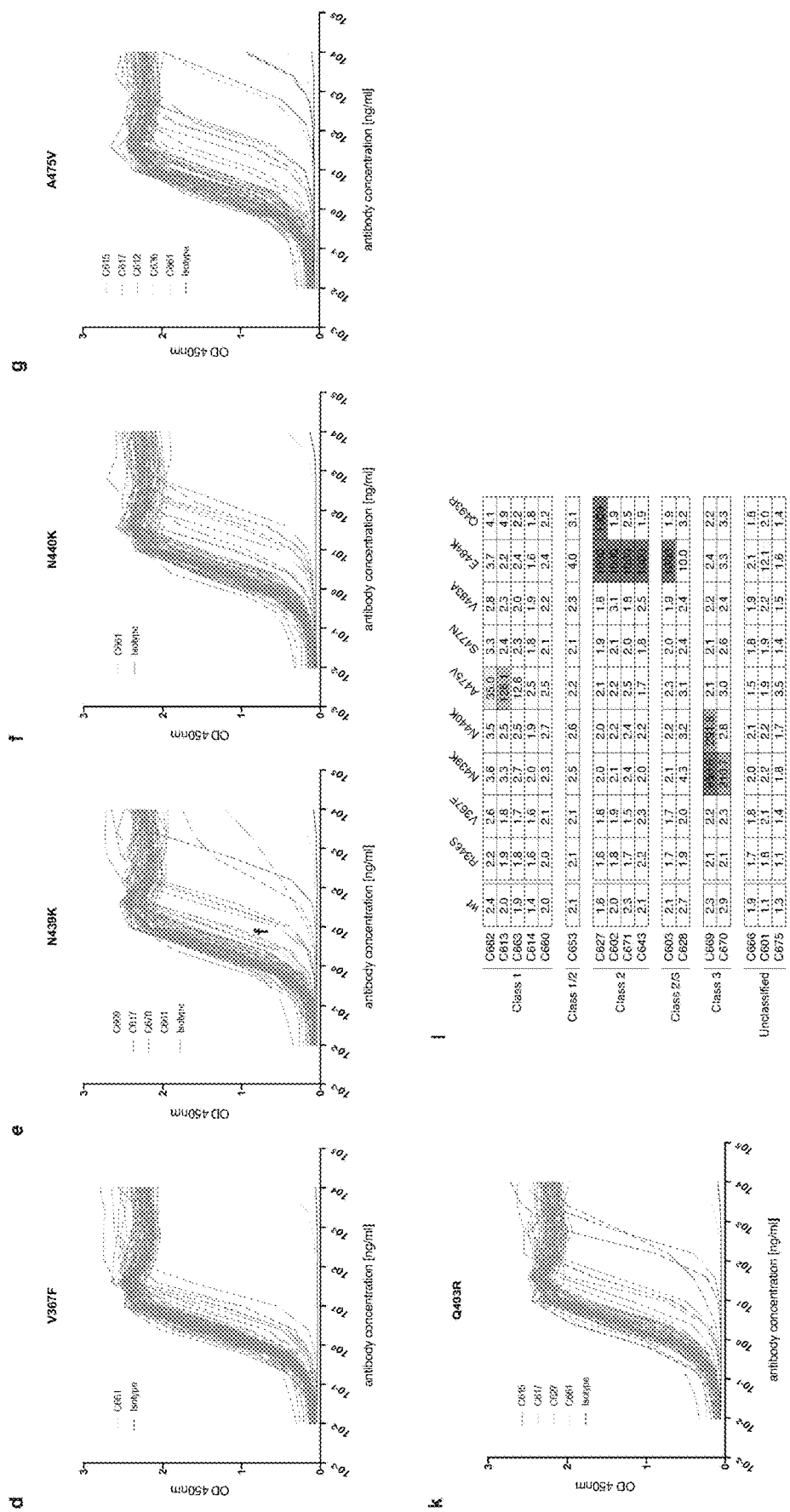

Eighty-four representative antibodies from 4 individuals were expressed and tested for reactivity to the RBD (Table 4). The antibodies included: (1) 58 that were randomly selected from those that appeared only once, and (2) 26 representatives of expanded clones. Of the antibodies tested 99% (83 out of the 84) bound to RBD, indicating that single-cell sorting by flow cytometry efficiently identified B cells producing anti-RBD antibodies (FIGS. 10a-b; Table 4). In anti-RBD ELISAs, the mean half-maximal effective concentration ($EC_{50}$) was higher than that observed in infected individuals after 6 months but not significantly different from antibodies obtained 1.3 months after infection (FIG. 6a; Table 4). To examine memory B cell antibodies for binding to circulating SARS-CoV-2 variants and antibody resistant mutants, ELISA assays were performed using mutant RBDs. Twenty-two (26%) of the antibodies showed at least 5-fold decreased binding to at least one of the mutant RBDs (FIGS. 10c-1; Table 4).

SARS-CoV-2 S pseudotyped viruses were used to measure the neutralizing activity of all 84 antibodies (FIG. 3a, Table 4). Consistent with the plasma neutralization results, the geometric mean neutralization half-maximal inhibitory concentration of the vaccinee antibodies ($IC_{50}$=151 ng/ml) was not significantly different from antibody collections obtained from naturally infected individuals 1.3 or 6.2 months after infection (FIG. 3a).

To examine the neutralizing breadth of the monoclonal antibodies and begin to map their target epitopes, the 17 most potent antibodies were tested, 8 of which carried IgHV3-53, against a panel of 12 SARS-CoV-2 variants: A475V is resistant to class 1 antibodies (structurally defined as described (Barnes, C. O. et al. Nature 588, 682-687 (2020)); E484K and Q493R are resistant to class 2 antibodies; while R346S, N439K, and N440K are resistant to class 3 antibodies. Additionally, K417N, Y453F, S477R, N501Y, D614G, and R683G represent circulating variants some of which have been associated with rapidly increasing case numbers. Based on their neutralizing activity against the variants, all but 3 of the antibodies were provisionally assigned to a defined antibody class or a combination (FIG. 3b). As seen in natural infection, a majority of the antibodies tested (9/17) were at least ten-fold less effective against pseudotyped viruses carrying the E484K mutation. In addition, 5 of the antibodies were less potent against K417N and 4 against N501Y by ten-fold or more (FIG. 3b).

To determine whether antibody-imposed selection pressure could also drive the emergence of resistance mutations in vitro, an rVSV/SARS-CoV-2 recombinant virus was cultured in the presence of each of 18 neutralizing monoclonal antibodies. All of the tested antibodies were selected for RBD mutations. Moreover, in all cases, the selected mutations corresponded to residues in the binding sites of their presumptive antibody class (FIG. 3c). For example, antibody 627, which was assigned to class 2 based on sensitivity to E484K mutation, was selected for the emergence of the E484K mutation in vitro (FIGS. 3b and c). Notably, 6 of the antibodies selected for K417N E or T, 5 selected for E484K and three selected for N501Y, T, or H, which coincide with mutations present in the circulating B1.1.17, 501Y. V2 and B1.1.28/501.V3 variants that have been associated with rapidly increasing case numbers in particular locales.

Antibody Epitopes

Cryo-EM Mapping of Antibody Epitopes

To further characterize antibody epitopes and mechanisms of neutralization, seven complexes between mAb Fab fragments and the prefusion, stabilized ectodomain trimer of SARS-CoV-2 S glycoprotein were characterized (Hsieh et al. Science: Vol. 369, Issue 6510, pp. 1501-1505 (2020)) using single-particle cryo-EM (FIG. 4). Fab-S complexes exhibited multiple RBD-binding orientations recognizing either 'up'/'down' (FIGS. 4a-j) or solely 'up' (FIGS. 4k-n) RBD conformations, consistent with structurally defined antibody classes from natural infection. The majority of mAbs characterized (6/7) recognized epitopes that included RBD residues involved in ACE2 recognition, suggesting a neutralization mechanism that directly blocks ACE2-RBD interactions. Additionally, structurally defined antibody epitopes were consistent with RBD positions that were selected in rVSV/SARS-CoV-2 recombinant virus outgrowth experiments, including K417, N439/N440, E484, and N501 (FIG. 3c and FIGS. 4f-j, 4m-n). Taken together, these data indicate that functionally similar antibodies are raised during vaccination and natural infection, and that the RBDs of spike trimers translated from the mRNA delivered by vaccination adopt a similar distribution of 'up'/'down' conformations as observed on SARS-CoV-2 virions.

Discussion

The mRNA-based SARS-CoV-2 vaccines are safe and effective and are being deployed globally to prevent infection and disease. The vaccine elicits antibody responses against the RBD, the major target of neutralizing antibodies in a manner that resembles natural infection. Notably, the neutralizing antibodies produced by mRNA vaccination target the same epitopes as natural infection. The data is consistent with SARS-CoV-2 spike trimers translated from the injected RNA adopting the range of conformations available to spikes on the surfaces of virions. Moreover, different individuals immunized with either the Moderna (mRNA-1273) or Pfizer-BioNTech (BNT162b2) vaccines produce closely related and nearly-identical antibodies.

Human neutralizing monoclonal antibodies to the SARS-CoV-2 RBD can be categorized as belonging to 4 different classes based on their target regions on the RBD. Class 1 and 2 antibodies are among the most potent and also the most abundant antibodies. These antibodies target epitopes that overlap or are closely associated with RBD residues K417, E484, and N501. They are frequently sensitive to mutations in these residues and select for K417N, E484K, and N501Y mutations in both yeast and VSV expressing SARS-CoV-2 S proteins. To avert selection and escape, antibody therapies should be composed of combinations of antibodies that target non-overlapping epitopes.

A number of circulating SARS-CoV-2 variants have been associated with rapidly increasing case numbers and have particular prevalence in the UK (B1.1.7/501Y.V1) and South Africa (501Y.V2), and Brazil (B1.1.28/501.V3). The experiments indicate that these variants, and potentially others that carry K417N/T, E484K, and N501Y mutations, can reduce the neutralization potency of vaccinee plasma. The comparatively modest effects of the mutations on viral sensitivity to plasma reflect the polyclonal nature of the neutralizing antibodies in vaccinee plasma. Nevertheless, emergence of these particular variants is consistent with the dominance of class 1 and 2 antibody response in infected or vaccinated individuals and raises the possibility that they emerged in response to immune selection in individuals with suboptimal immunity. The data indicate that SARS-CoV-2 vaccines may need to be updated and immunity monitored in order to compensate for viral evolution.

Lengthy table referenced here

US12060411-20240813-T00001

Please refer to the end of the specification for access instructions.

Lengthy table referenced here

US12060411-20240813-T00002

Please refer to the end of the specification for access instructions.

Lengthy table referenced here

US12060411-20240813-T00003

Please refer to the end of the specification for access instructions.

Lengthy table referenced here

US12060411-20240813-T00004

Please refer to the end of the specification for access instructions.

Lengthy table referenced here

US12060411-20240813-T00005

Please refer to the end of the specification for access instructions.

Lengthy table referenced here

US12060411-20240813-T00006

Please refer to the end of the specification for access instructions.

Lengthy table referenced here
US12060411-20240813-T00007

Please refer to the end of the specification for access instructions.

Lengthy table referenced here
US12060411-20240813-T00008

Please refer to the end of the specification for access instructions.

Lengthy table referenced here
US12060411-20240813-T00009

Please refer to the end of the specification for access instructions.

Lengthy table referenced here
US12060411-20240813-T00010

Please refer to the end of the specification for access instructions.

Lengthy table referenced here
US12060411-20240813-T00011

Please refer to the end of the specification for access instructions.

Lengthy table referenced here
US12060411-20240813-T00012

Please refer to the end of the specification for access instructions.

Lengthy table referenced here
US12060411-20240813-T00013

Please refer to the end of the specification for access instructions.

Lengthy table referenced here
US12060411-20240813-T00014

Please refer to the end of the specification for access instructions.

Lengthy table referenced here
US12060411-20240813-T00015

Please refer to the end of the specification for access instructions.

Lengthy table referenced here
US12060411-20240813-T00016

Please refer to the end of the specification for access instructions.

Lengthy table referenced here
US12060411-20240813-T00017

Please refer to the end of the specification for access instructions.

Lengthy table referenced here
US12060411-20240813-T00018

Please refer to the end of the specification for access instructions.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

LENGTHY TABLES

The patent contains a lengthy table section. A copy of the table is available in electronic form from the USPTO web site (https://seqdata.uspto.gov/?pageRequest=docDetail&DocID=US12060411B2). An electronic copy of the table will also be available from the USPTO upon request and payment of the fee set forth in 37 CFR 1.19(b)(3).

SEQUENCE LISTING

The patent contains a lengthy sequence listing. A copy of the sequence listing is available in electronic form from the USPTO web site (https://seqdata.uspto.gov/?pageRequest=docDetail&DocID=US12060411B2). An electronic copy of the sequence listing will also be available from the USPTO upon request and payment of the fee set forth in 37 CFR 1.19(b)(3).

What is claimed is:

1. An isolated anti-SARS-CoV-2 antibody or antigen-binding fragment thereof that binds specifically to a SARS-CoV-2 antigen, comprising three heavy chain complementarity determining regions (HCDRs) (HCDR1, HCDR2, and HCDR3) of a heavy chain variable region having the amino acid sequence of SEQ ID NO: 1 and three light chain CDRs (LCDR1, LCDR2, and LCDR3) of a light chain variable region having the amino acid sequence of SEQ ID NO: 2.

2. The antibody or antigen-binding fragment thereof of claim 1, wherein the SARS-CoV-2 antigen comprises a Spike (S) polypeptide.

3. The antibody or antigen-binding fragment thereof of claim 1, wherein the antibody or antigen-binding fragment thereof is capable of neutralizing a plurality of SARS-CoV-2 strains.

4. The antibody or antigen-binding fragment thereof of claim 1, wherein the anti-SARS-CoV-2 antibody or antigen-binding fragment thereof comprises a heavy chain variable region of SEQ ID NO: 1 and a light chain variable region of SEQ ID NO: 2.

5. The antibody or antigen-binding fragment thereof of claim 1, wherein the antibody or antigen-binding fragment thereof is a multivalent antibody comprising (a) a first target binding site comprising three heavy chain complementarity determining regions (HCDRs) (HCDR1, HCDR2, and HCDR3) of a heavy chain variable region having the amino acid sequence of SEQ ID NO: 1 and three light chain CDRs (LCDR1, LCDR2, and LCDR3) of a light chain variable region having the amino acid sequence of SEQ ID NO: 2 that specifically binds to an epitope within the S polypeptide, and (b) a second target binding site that binds to an epitope on a different epitope on the S polypeptide or a different molecule.

6. The antibody or antigen-binding fragment thereof of claim 5, wherein the multivalent antibody is a bivalent or bispecific antibody.

7. The antibody or the antigen-binding fragment thereof of claim 1, further comprising an Fc region or a variant Fc region.

8. The antibody or antigen-binding fragment thereof of claim 1, wherein the antibody is a monoclonal antibody.

9. The antibody or antigen-binding fragment thereof of claim 1, wherein the antibody is a chimeric antibody, a humanized antibody, or humanized monoclonal antibody.

10. The antibody or antigen-binding fragment thereof of claim 1, wherein the antibody is a single-chain antibody, a Fab fragment, or a Fab2 fragment.

11. A pharmaceutical composition comprising the antibody or antigen-binding fragment thereof of claim 1 and optionally a pharmaceutically acceptable carrier or excipient.

12. The pharmaceutical composition of claim 11, further comprising a second therapeutic agent.

13. The pharmaceutical composition of claim 12, wherein the second therapeutic agent comprises an anti-inflammatory drug or an antiviral compound.

14. A kit comprising the pharmaceutical composition of claim 11 for the diagnosis, prophylaxis, treatment, or combination thereof of a condition resulting from a SARS-CoV-2 infection.

15. A nucleic acid molecule encoding a polypeptide chain of the antibody or antigen-binding fragment thereof of claim 1.

16. A vector comprising the nucleic acid molecule of claim 15.

17. A cultured host cell comprising the nucleic acid molecule of claim 15.

18. A method of preparing an antibody, or antigen-binding portion thereof, comprising:
    obtaining the cultured host cell of claim 17;
    culturing the cultured host cell in a medium under conditions permitting expression of a polypeptide encoded by the nucleic acid molecule and assembling of an antibody or fragment thereof; and
    purifying the antibody or fragment from the cultured cell or the medium of the cell.

19. A kit comprising a pharmaceutically acceptable dose unit of the antibody or antigen-binding fragment thereof of claim 1.

20. A kit for the diagnosis, prognosis or monitoring the treatment of SARS-CoV-2 infection in a subject, comprising: the antibody or antigen-binding fragment thereof of claim 1; and at least one detection reagent that binds specifically to the antibody or antigen-binding fragment thereof.

21. A method of neutralizing SARS-CoV-2 in a subject, comprising administering to a subject in need thereof a therapeutically effective amount of the antibody or antigen-binding fragment thereof of claim 1.

22. A method of treating a SARS-CoV-2 infection, comprising administering to a subject in need thereof a therapeutically effective amount of the antibody or antigen-binding fragment thereof of claim 1.

23. The method of claim 22, further comprising administering to the subject a therapeutically effective amount of a second therapeutic agent or therapy.

24. The method of claim 23, wherein the second therapeutic agent comprises an anti-inflammatory drug or an antiviral compound.

25. The method of claim 21, wherein the antibody or antigen-binding fragment thereof is administered to the subject intravenously, subcutaneously, or intraperitoneally.

26. The method of claim 21, wherein the antibody or antigen-binding fragment thereof is administered prophylactically or therapeutically.

27. A method for detecting the presence of SARS COV-2 in a sample comprising:
- contacting a sample with the antibody or antigen-binding fragment thereof of claim 1; and
- determining binding of the antibody or antigen-binding fragment to one or more SARS CoV-2 antigens,
- wherein binding of the antibody to the one or more SARS CoV-2 antigens is indicative of the presence of SARS CoV-2 in the sample.

* * * * *